United States Patent
Sung et al.

(10) Patent No.: US 9,658,348 B2
(45) Date of Patent: May 23, 2017

(54) X-RAY DETECTOR, X-RAY IMAGING APPARATUS HAVING THE SAME, AND METHOD OF CONTROLLING THE SAME

(71) Applicant: SAMSUNG ELECTRONICS CO., LTD., Suwon-si (KR)

(72) Inventors: Young Hun Sung, Hwaseong-si (KR); Jae Hak Lee, Yongin-si (KR); Dong Goo Kang, Hwaseong-si (KR); Jae Mock Yi, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 205 days.

(21) Appl. No.: 14/554,905

(22) Filed: Nov. 26, 2014

(65) Prior Publication Data

US 2015/0146852 A1 May 28, 2015

(30) Foreign Application Priority Data

Nov. 27, 2013 (KR) .................. 10-2013-0145574

(51) Int. Cl.
*H05G 1/56* (2006.01)
*G01T 1/29* (2006.01)
(Continued)

(52) U.S. Cl.
CPC .......... *G01T 1/2921* (2013.01); *G01N 23/04* (2013.01); *H04N 5/32* (2013.01); *H04N 5/3454* (2013.01); *H04N 5/378* (2013.01); *H04N 5/3745* (2013.01)

(58) Field of Classification Search
CPC .......... H04N 5/32; H04N 5/321; G01N 23/02; G01N 23/04; G01N 23/043; G01N 23/08;
(Continued)

(56) References Cited

U.S. PATENT DOCUMENTS 8,445,878 B2 * 5/2013 Guez .................. A44C 5/20
250/396 R
2010/0272238 A1 10/2010 Machan et al.
(Continued)

FOREIGN PATENT DOCUMENTS

EP 2665257 A1 11/2013
JP 2001-249183 A 9/2001
(Continued)

OTHER PUBLICATIONS

Communication dated Apr. 16, 2015, issued by the European Patent Office in counterpart European Application No. 14195134.3.

*Primary Examiner* — Jurie Yun
(74) *Attorney, Agent, or Firm* — Sughrue Mion, PLLC

(57) ABSTRACT

An X-ray detector capable of independently controlling a read-out rate for each region, an X-ray imaging apparatus having the same, and a method of controlling the same are provided. The X-ray detector includes a plurality of pixels which are two-dimensionally arranged and configured to output an electrical signal corresponding to incident X-rays, a plurality of gate lines configured to connect the plurality of pixels in a row direction, a plurality of data lines configured to connect the plurality of pixels in a column direction, a read-out circuit configured to read out the electrical signal generated by the plurality of pixels through the plurality of data lines, and a switcher configured to independently turn connections between the respective data lines in the plurality of data lines and the read-out circuit on and off.

24 Claims, 20 Drawing Sheets

(51) Int. Cl.
  *G01N 23/04* (2006.01)
  *H04N 5/32* (2006.01)
  *H04N 5/345* (2011.01)
  *H04N 5/3745* (2011.01)
  *H04N 5/378* (2011.01)

(58) Field of Classification Search
  CPC .. G01N 23/083; A61B 6/4208; A61B 6/4233; G01T 1/2921; G01T 1/2928; H05G 1/56; H05G 1/58
  USPC ............ 378/42, 62, 98.8, 114–116; 250/394
  See application file for complete search history.

(56) References Cited

U.S. PATENT DOCUMENTS

2011/0026676 A1    2/2011  Takekoshi
2013/0308031 A1*  11/2013  Theuwissen ......... H04N 5/3454
                                                       348/308

FOREIGN PATENT DOCUMENTS

| JP | 2013-42788 A     | 3/2013  |
| JP | 2013-106990 A    | 6/2013  |
| KR | 10-2006-0112784 A | 11/2006 |
| KR | 10-2012-0041360 A | 5/2012  |
| WO | 2013/011914 A1   | 1/2013  |
| WO | 2013/150884 A1   | 10/2013 |

\* cited by examiner

FIG. 1

| | (1,1) | (1,2) | (1,3) | (1,4) | (1,5) | .... | (1,m) |
|---|---|---|---|---|---|---|---|
| | (2,1) | (2,2) | (2,3) | (2,4) | (2,5) | .... | |
| | (3,1) | (3,2) | (3,3) | (3,4) | (3,5) | .... | |
| n | (4,1) | (4,2) | (4,3) | (4,4) | (4,5) | .... | |
| | (5,1) | (5,2) | (5,3) | (5,4) | (5,5) | .... | |
| | ⋮ | ⋮ | ⋮ | ⋮ | ⋮ | .... | |
| | (n,1) | (n,2) | (n,3) | (n,4) | (n,5) | | (n,m) |

⟋⟋ : ROI PIXEL

☐ : BACKGROUND PIXEL

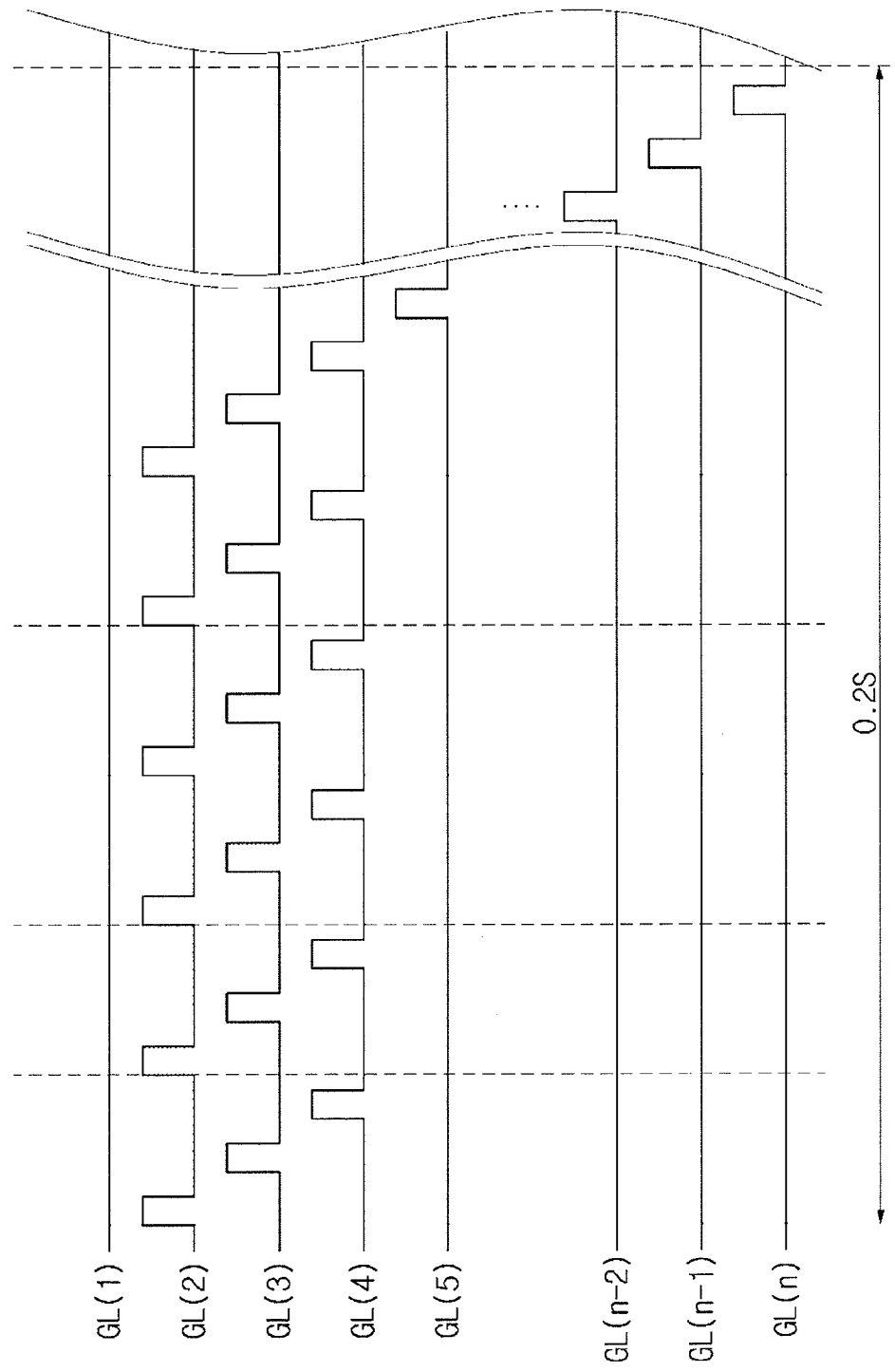

FIG. 14
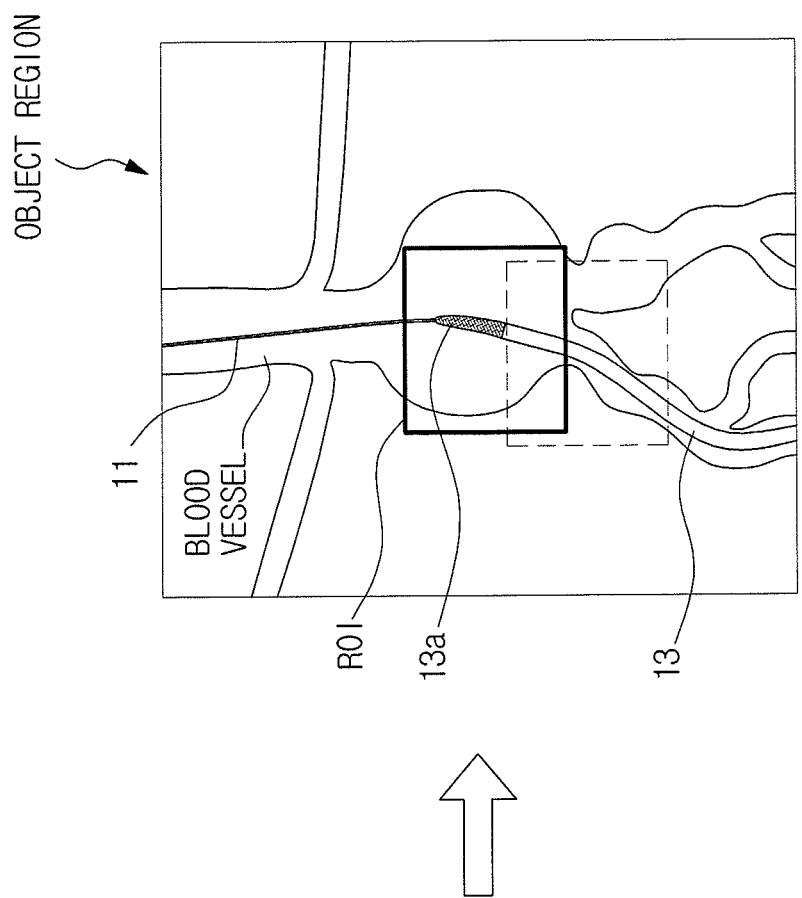
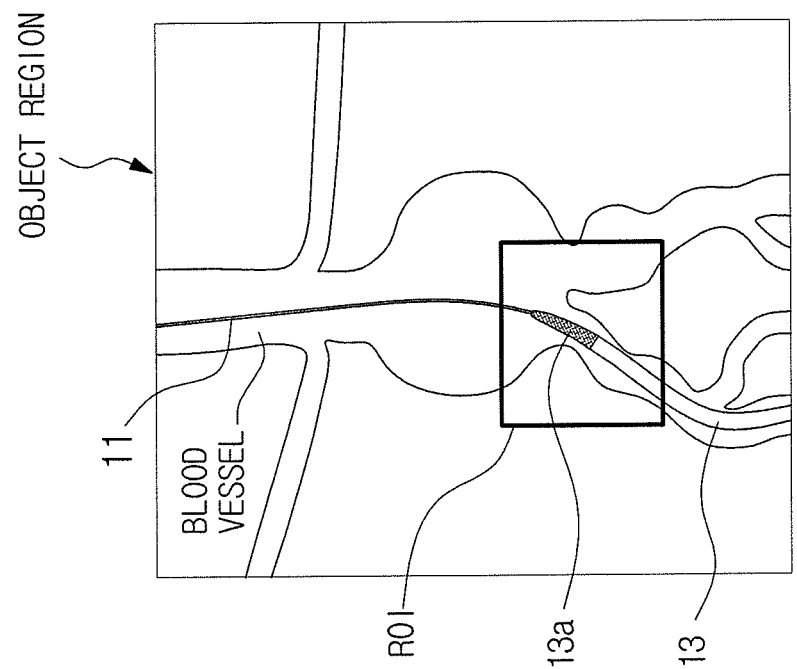

X-RAY DETECTOR, X-RAY IMAGING APPARATUS HAVING THE SAME, AND METHOD OF CONTROLLING THE SAME

CROSS-REFERENCE TO RELATED APPLICATION

This application claims the benefit of Korean Patent Application No. 10-2013-0145574, filed on Nov. 27, 2013 in the Korean Intellectual Property Office, the disclosure of which is incorporated herein by reference in its entirety.

BACKGROUND

1. Field

Exemplary embodiments of the present disclosure relate to an X-ray detector configured to radiate X-rays onto an object and image an inside of the object, an X-ray imaging apparatus having the same, and a method of controlling the same.

2. Description of the Related Art

An X-ray imaging apparatus is an apparatus capable of obtaining an internal image of an object by radiating X-rays onto the object and using X-rays transmitted through the object to obtain the internal image. Since permeability of X-rays differs depending on properties of a substance composing the object, it is possible to image an internal structure of the object using an intensity or strength of X-rays transmitted through the object.

Recently, X-ray video technology capable of observing movement occurring inside the object has been developed and applied to an intervention procedure such as angiography or the field of X-ray imaging such as fluoroscopy.

The internal image of the object may be divided into a region of interest (ROI) that is a region which a user is interested in observing and a background that is a region other than the ROI. Since the ROI and the background may have different conditions necessary for obtaining images thereof, technology capable of independently controlling these regions needs to be developed.

SUMMARY

The exemplary embodiments may provide an X-ray detector capable of independently controlling a read-out rate for each region, an X-ray imaging apparatus having the same, and a method of controlling the same.

According to an aspect of an exemplary embodiment, there is provided an X-ray detector including a plurality of pixels which are two-dimensionally arranged and configured to output an electrical signal corresponding to incident X-rays, a plurality of gate lines configured to connect the plurality of pixels in a row direction, a plurality of data lines configured to connect the plurality of pixels in a column direction, a read-out circuit configured to read out the electrical signal generated by the plurality of pixels through the plurality of data lines, and a switcher configured to independently turn connections between the respective data lines in the plurality of data lines and the read-out circuit on and off.

The X-ray detector may further include a gate driver configured to apply an on signal to the plurality of gate lines and a switch driver configured to apply an on signal to the switcher.

The switcher may include a plurality of switching elements configured to be respectively connected to each of the plurality of data lines.

The gate driver may be configured to apply an on signal to a gate line corresponding to a region of interest (ROI) among the plurality of gate lines, in order to obtain a frame image of the ROI.

The switch driver may be configured to apply an on signal to a switching element to which a data line corresponding to the ROI is connected in order to obtain the frame image of the ROI.

The on signal applied to the gate line and the on signal applied to the switching element may be synchronized with each other.

The X-ray detector may further include a detector controller configured to control a timing of the on signal output from the gate driver and the switch driver based on information on the ROI.

The detector controller may be configured to control the gate driver and the switch driver such that the frame image of the ROI is obtained at a read-out rate higher than a read-out rate used to obtain a frame image of a background surrounding the ROI.

According to another aspect of an exemplary embodiment, there is provided an X-ray imaging apparatus. The X-ray imaging apparatus includes an X-ray source configured to radiate X-rays onto an object, an X-ray detector according to an aspect of an exemplary embodiment, and an image processor configured to obtain information on a region of interest (ROI) from the frame image obtained by the X-ray detector and deliver the information on the ROI to the X-ray detector.

The image processor may be configured to detect an object of interest from the frame image and set the ROI based on a position, a size, or a movement characteristic of the object of interest.

The information on the ROI may include at least one of a position of the ROI, a size of the ROI, and a movement characteristic of the ROI.

The image processor may detect the object of interest and set the ROI in real time.

The X-ray imaging apparatus may further include an ROI filter provided between the X-ray source and the X-ray detector and configured to filter the X-rays, a filter driver configured to move the ROI filter, and a controller configured to control the filter driver such that the ROI filter moves to a position corresponding to a background of the frame image.

The X-ray detector may further include a gate driver configured to apply an on signal to the plurality of gate lines and a switch driver configured to apply an on signal to the switching unit.

The X-ray detector may further include a detector controller configured to control a timing of the on signal output from the gate driver and the on signal output from the switch driver based on the information on the ROI and read-out rates to be applied to the ROI and the background.

The controller may be configured to set a read-out rate to be applied to the ROI based on the information on the ROI and deliver information on the set read-out rate to the detector controller.

The controller may set a read-out rate to be applied to the background based on an X-ray dose incident on the background and deliver information on the set read-out rate to the detector controller.

According to still another aspect of an exemplary embodiment, there is provided a method of controlling an X-ray detector including a plurality of pixels which are two-dimensionally arranged and output an electric signal corresponding to incident X-rays. The method includes receiving information on a region of interest (ROI), obtaining a frame image of the ROI at a first read-out rate, and obtaining a frame image of a background surrounding the ROI at a second read-out rate that is different from the first read-out rate.

The X-ray detector may further include a plurality of gate lines configured to connect the plurality of pixels in a row direction, a plurality of data lines configured to connect the plurality of pixels in a column direction, a read-out circuit configured to read out the electrical signal generated by the plurality of pixels through the plurality of data lines, and a plurality of switching elements connected to each of the plurality of data lines and configured to independently turn connections between the respective data lines in the plurality of data lines and the read-out circuit on and off.

The obtaining of the frame image of the ROI may include applying an on signal to a gate line corresponding to the ROI, among the plurality of gate lines, at the first read-out rate, and applying an on signal to a switching element to which a data line corresponding to the ROI is connected, among the plurality of data lines.

The obtaining of the frame image of the background may include applying an on signal to a gate line corresponding to the background at the second read-out rate and applying an on signal to a second switching element to which a data line corresponding to the background is connected.

The first read-out rate may have a value greater than the second read-out rate.

According to yet another aspect of an exemplary embodiment, there is provided a method of controlling an X-ray imaging apparatus. The method includes radiating X-rays onto an object, detecting X-rays transmitted through the object among the radiated X-rays and obtaining a frame image of the object based on the detected X-rays, obtaining information on a region of interest (ROI) from the frame image of the object, and obtaining a frame image of the ROI and a frame image of a background surrounding the ROI at different read-out rates.

The method may further include setting a read-out rate to be applied to the ROI based on the information on the ROI.

The method may further include filtering the radiated X-rays which are incident on the background.

The method may further include setting a read-out rate to be applied to the background based on an X-ray dose incident on the background.

The information on the ROI may include a movement size of the ROI, and the setting of the read-out rate to be applied to the ROI may include setting the higher read-out rate to be applied to the ROI as the movement size of the ROI becomes greater.

The setting of the read-out rate to be applied to the background may include setting the lower read-out rate to be applied to the background as an X-ray dose incident on the background becomes lower.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which:

FIG. 1 is a diagram schematically illustrating a pixel structure included in an X-ray detector according to an exemplary embodiment;

FIG. 5 is another timing diagram illustrating an operation of obtaining an electrical signal of the X-ray detector according to an exemplary embodiment;

FIG. 14 is a diagram illustrating movement of the ROI according to movement of an object of interest;

DETAILED DESCRIPTION

Hereinafter, exemplary embodiments of an X-ray detector, an X-ray imaging apparatus having the same, and a method of controlling the same will be described in detail with reference to the accompanying drawings.

An X-ray image is an image of a region of an object through which X-rays are transmitted and detected, among internal regions of the object. Users such as a doctor or a radiologist may require information on only a certain region of the X-ray image or may wish to observe a certain region more carefully. Hereinafter, in the exemplary embodiment to be described, the certain region may be referred to as a region of interest (ROI) and a region other than the ROI may be referred to as a background. According to an exemplary embodiment, the background typically surrounds the ROI.

Figure 1:
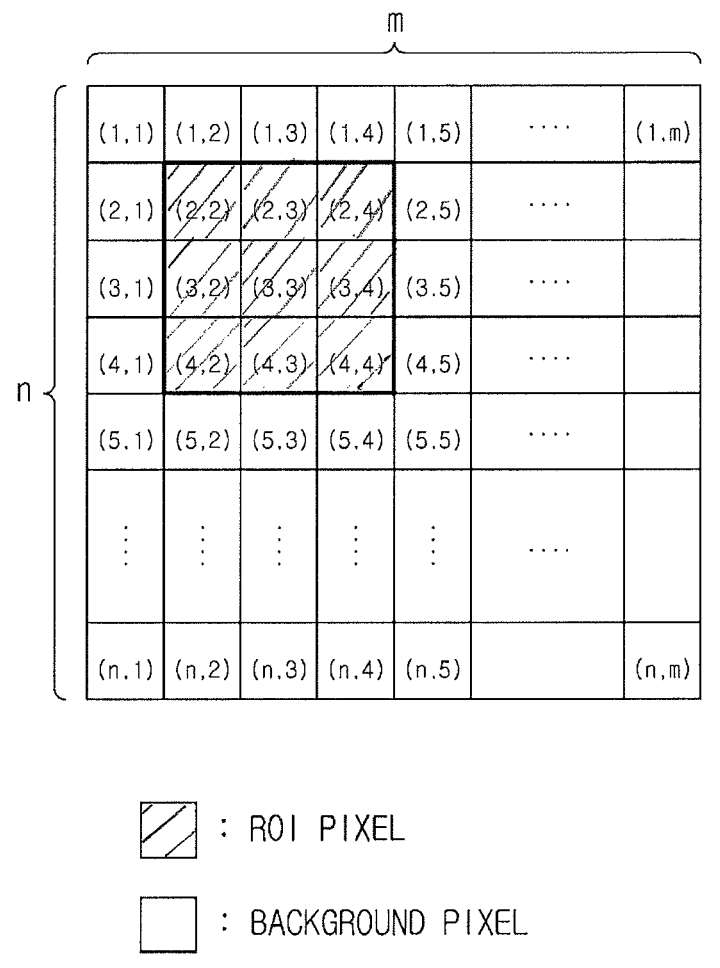
Figure 2:
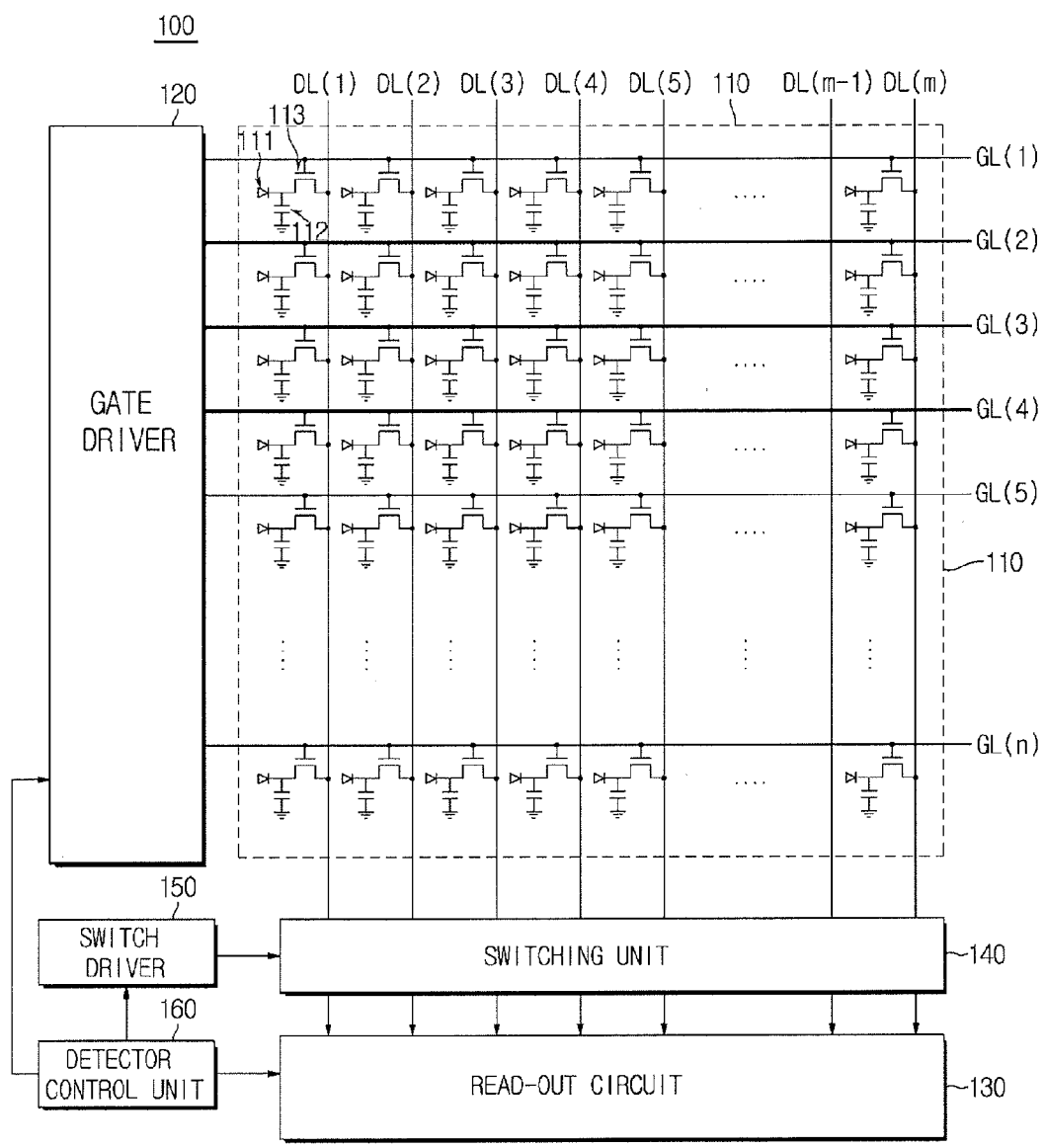
FIG. 2 is a diagram schematically illustrating a configuration of the X-ray detector according to an exemplary embodiment.

FIG. 1 is a diagram schematically illustrating a pixel structure included in an X-ray detector according to an exemplary embodiment. FIG. 2 is a diagram schematically illustrating a configuration of the X-ray detector according to the exemplary embodiment.

As illustrated in FIG. 1, when the X-ray detector includes two-dimensionally arranged n×m (m and n are integers of 2 or more) pixels, some of the pixels may be set as an ROI. In an example in FIG. 1, for convenience of description, 3×3 pixels are set as an ROI. A position of an individual pixel may be represented in matrix coordinates. The ROI pixels include pixels in positions (2,2), (2,3), (2,4), (3,2), (3,3), (3,4), (4,2), (4,3), and (4,4), and the remaining pixels are background pixels.

The ROI may be directly set by a user or may be autonomously set by the X-ray imaging apparatus according to pre-stored information. Setting of the ROI will be described in detail in the exemplary embodiment of the X-ray imaging apparatus.

In the field of X-ray diagnosis or X-ray operation such as angiography and fluoroscopy, when an X-ray video is imaged, it is possible to capture movement inside the ROI more precisely if an image of the ROI is obtained at a high read-out rate.

However, since there is little movement in the background, and since such little movement in the background is not of interest, the necessity of applying a high read-out rate is low. Also, when a relatively low read-out rate is applied to the background, an X-ray dose used for obtaining a single frame image increases, thereby improving a quality of the image.

Since existing X-ray detectors are unable to independently adjust a read-out rate for each pixel, read-out rates of the ROI and the background cannot be adjusted to be different from each other. However, the X-ray detector according to an exemplary embodiment has a structure in which a read-out rate for each pixel can be independently adjusted. Hereinafter, the structure of the X-ray detector according to an exemplary embodiment will be described in detail with reference to FIG. 2.

As illustrated in FIG. 2, an X-ray detector 100 according to an exemplary embodiment includes a detection region 110 that is a region in which X-rays are detected and the detected X-rays are converted into an electrical signal, a gate driver 120 configured to transmit an on and off signal for indicating a signal read-out to the detection region 110, a read-out circuit 130 configured to read out an electrical signal corresponding to an intensity of X-rays from the detection region 110, a switching unit 140 (e.g., switcher) configured to turn a connection between the detection region 110 and the read-out circuit 130 on and off, a switch driver 150 configured to transmit an on and off signal to the switching unit 140, and a detector control unit 160 (e.g., detector controller) configured to control the gate driver 120 and the switch driver 150.

A method of converting the X-rays detected in the detection region 110 into an electrical signal includes, for example, a direct converting method and an indirect converting method, and may include other conversion methods known to those skilled in the art.

In the direct converting method, when X-rays are incident on the detection region 110, electron-hole pairs are temporarily generated inside a light receiving element included in the detection region 110, electrons move to the anode and holes move to the cathode due to an electric field applied to both ends of the light receiving element, and the read-out circuit 130 reads out a flow of the electrons or holes as an electrical signal. In the direct converting method, a photoconductor such as amorphous selenium (a-Se), CdZnTe, HgI2, and PbI2 may be used as the light receiving element.

In the indirect converting method, the detection region 110 further includes a scintillator. When the incident X-rays react with the scintillator and are converted into visible light, the light receiving element detects the converted visible light and converts the light into an electrical signal. In the indirect converting method, a photodiode such as amorphous silicon (a-Si) may be used as the light receiving element, and a thin-film GADOX scintillator, or a micro columnar or needle-shaped CSI (T1) scintillator may be used as the scintillator.

According to an exemplary embodiment, any of the direct converting method and the indirect converting method may be used. The following example of an exemplary embodiment which applies the indirect converting method will be described.

The detection region 110 includes two-dimensionally arranged n×m pixels as in the example of FIG. 1. Each pixel includes a photodiode 111 in which electric charge corresponding to an intensity of incident X-rays is generated, a capacitor 112 configured to store the generated electric charge, and a first switching element 113 configured to turn a flow of the electric charge stored in the capacitor 112 along a data line DL on and off.

The X-rays which are incident on the X-ray detector 100 are converted into visible light by the scintillator (not illustrated). When the converted visible light reaches the photodiode 111, the photodiode 111 generates electric charge having an amount corresponding to an intensity of the visible light. The generated electric charge is stored in the capacitor 112.

When an on signal is input to the first switching element 113, that is, when the first switching element 113 is turned on, the electric charge stored in the capacitor 112 flows along the data line DL. When no on signal is input, the first switching element 113 maintains an off state and electric charge is accumulated in the capacitor 112.

A transistor may be used as an example of the first switching element 113, and a thin film transistor (TFT) may be used in the exemplary embodiment of FIG. 2. Therefore, when a voltage signal of a predetermined level or more is applied to a gate of the first switching element 113, the electric charge stored in the capacitor 112 flows from a source to a drain of the first switching element 113. The voltage signal applied to the gate in order to turn the first switching element 113 on is referred to as an on signal or gate signal.

The first switching elements 113 are connected to a gate line GL for each row and are connected to a data line DL for each column. In the example of FIG. 2, m first switching elements 113 arranged in the same row are connected to a single gate line GL and n first switching elements 113 arranged in the same column are connected to a single data line DL.

The gate driver 120 sequentially applies the gate signal to n gate lines GL(1), GL(2), . . . , and GL(n). When the gate driver 120 applies the gate signal, that is, the on signal, to the gate line GL, m first switching elements 113 connected to a corresponding gate line are turned on and the electric charge stored in the capacitor 112 of a corresponding pixel flows to the data line DL through the first switching element 113. That is, the X-ray detector 100 obtains an X-ray image through a line scan.

The electrical signal delivered through m data lines DL(1), DL(2), . . . , and DL(m) is input to the read-out circuit

130. The switching unit 140 is provided at an end of the data line, that is, between the detection region 110 and the read-out circuit 130, and selectively turns a connection between the data line and the read-out circuit 130 on and off. By providing the switching unit 140 between the data lines DL(1), DL(2) . . . DL(m) and the read-out circuit 130, the read-out circuit 130 can independently read data from each pixel. Thus, the configuration including the switching unit 140 according to exemplary embodiments may achieve significant advantages not achieved by related art configurations.

When the switch driver 150 applies the on signal to the switching unit 140 and the switching unit 140 is turned on, the electrical signal delivered from the detection region 110 is input to the read-out circuit 130, and when the switching unit 140 is in an off state, no electrical signal is input to the read-out circuit 130.

The switching unit 140 is able to independently turn connections with the read-out circuit 130 on and off for each of m data lines. Hereinafter, configurations of the switching unit 140 and the read-out circuit 130 will be described with reference to FIG. 3.

Figure 3:
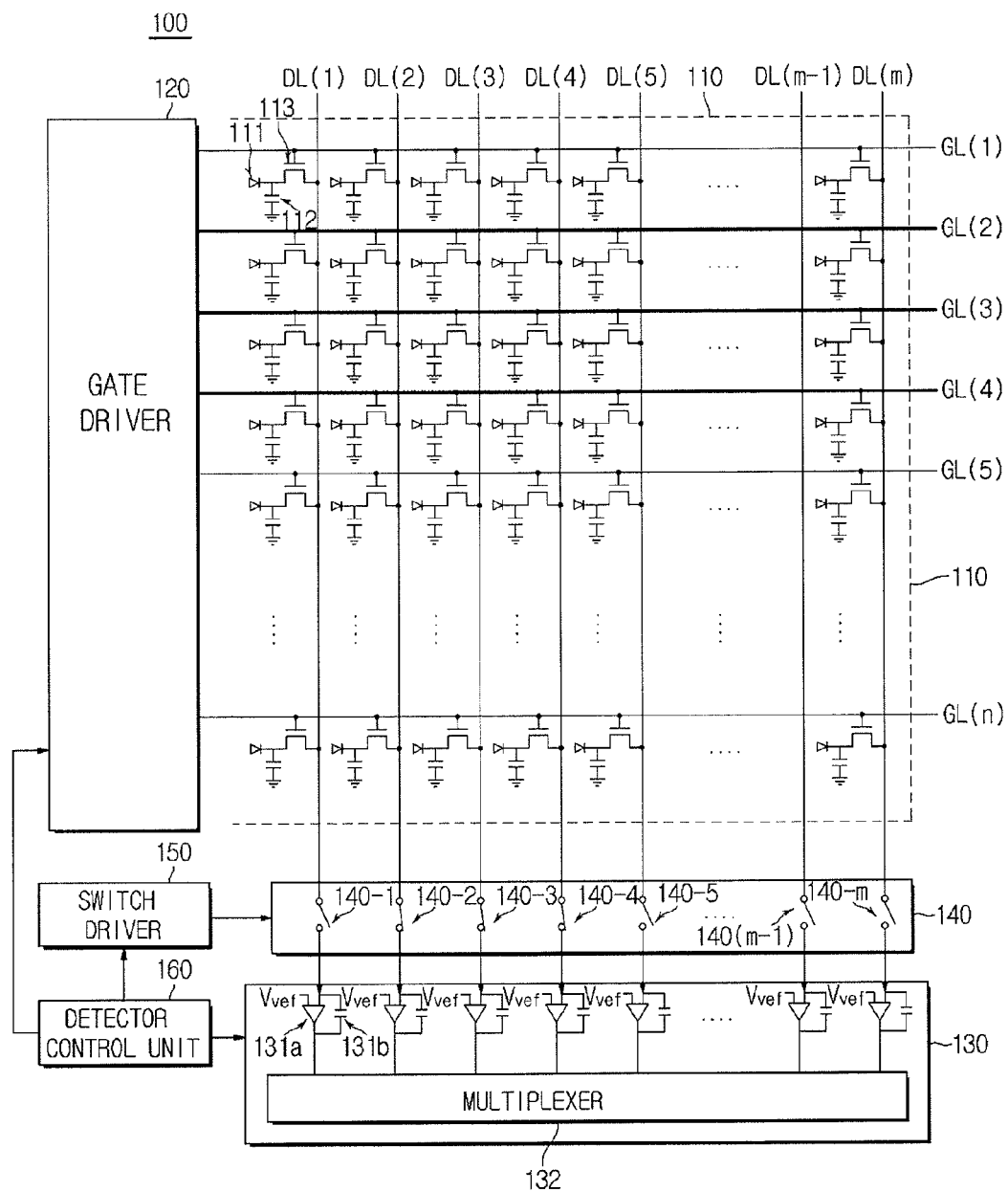
FIG. 3 is a diagram schematically illustrating a configuration of a switching unit and a read-out circuit of the X-ray detector according to an exemplary embodiment.

FIG. 3 is a diagram schematically illustrating a configuration of a switching unit and a read-out circuit of the X-ray detector according to an exemplary embodiment.

As illustrated in FIG. 3, the switching unit 140 may include m second switching elements 140-1, 140-2, . . . , and 140-m corresponding to each of m data lines. The second switching element is closed when the on signal is input and is opened when no on signal is input. The second switching element may be implemented as many different types of switching elements according to exemplary embodiments. For example, a semiconductor device such as a transistor and/or a thyristor may be used as the second switching element.

The switch driver 150 may individually turn m second switching elements on and off. Accordingly, it is possible to individually turn connections with the read-out circuit 130 on and off for each of m data lines. When the on signal is input to the gate line corresponding to the ROI and the data line corresponding to the ROI is connected to the read-out circuit 130, the electrical signal may be read out from the pixel corresponding to the ROI.

The gate line corresponding to the ROI is a gate line to which the pixel corresponding to the ROI is connected. When there is a pixel corresponding to the ROI out of m pixels connected to a single gate line, the gate line may be considered a gate line corresponding to the ROI.

Similarly, the data line corresponding to the ROI is a data line to which the pixel corresponding to the ROI is connected. When there is a pixel corresponding to the ROI out of n pixels connected to a single data line, the data line may be considered a data line corresponding to the ROI.

Specifically, when the ROI is represented as in FIG. 2, that is, when pixels in positions (2,2), (2,3), (2,4), (3,2), (3,3), (3,4), (4,2), (4,3), and (4,4) correspond to the ROI, the gate driver 120 applies an on signal to GL(2), and the switch driver 150 applies an on signal to the second switching elements 140-2, 140-3, and 140-4 connected to DL(2), DL(3), and DL(4).

When the on signal is input to the gate of the first switching element 113 but the second switching element connected to the data line is opened, the electric charge stored in the capacitor 112 is not discharged. Accordingly, the electric charge stored in the capacitor 112 is discharged along the data line only in pixels connected to DL(2), DL(3), and DL(4) out of pixels connected to GL(2), that is, pixels in positions (2,2), (2,3), and (2,4), and in the remaining pixels, the electric charge is accumulated in the capacitor 112.

Then, the on signal is sequentially applied to GL(3) and GL(4), and the on signal is applied to the second switching elements 140-2, 140-3, and 140-4. The on signal applied to the gate line and the on signal applied to the second switching element may be synchronized.

As described above, since the electrical signal for each pixel can be independently read out, it is also possible to independently control a read-out rate for each region. Control of the read-out rate will be specifically described below with reference to FIGS. 4A and 4B.

The read-out circuit 130 includes m amplifiers 131a corresponding to each of m data lines and a capacitor 131b connected to an input end and an output end of each amplifier 131a.

The amplifier 131a includes a first input end connected to the switching unit 140, a second input end to which a reference voltage (Vref) is applied, and an output end. For example, the first input end may be a negative terminal of the amplifier 131a and the second input end may be a positive terminal of the amplifier 131a. The output end is connected to a multiplexer 132.

An end of the capacitor 131b is connected to the first input end of the amplifier 131a and the other end thereof is connected to an output end of the amplifier 131a. Also, although not illustrated, the ends of the capacitor 131b are connected by a switch and thereby a voltage charged in the capacitor 131b may be discharged.

The electrical signal output from the amplifier 131a is input to the multiplexer 132 and the multiplexer 132 sequentially delivers the input electrical signal to an external image processing unit (e.g., external image processor). For this purpose, the multiplexer 132 may include switches corresponding to each amplifier 131a.

Figure 4A:
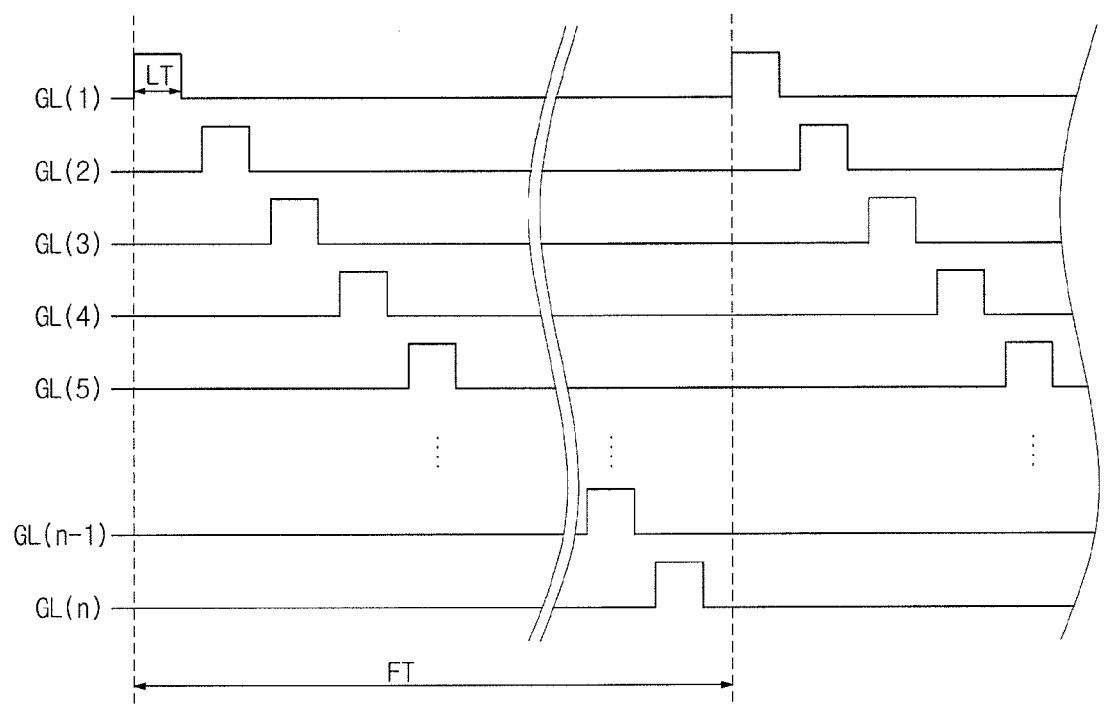
FIG. 4A is a timing diagram illustrating an operation of obtaining an electrical signal at the same read-out rate for all pixels.
Figure 4B:
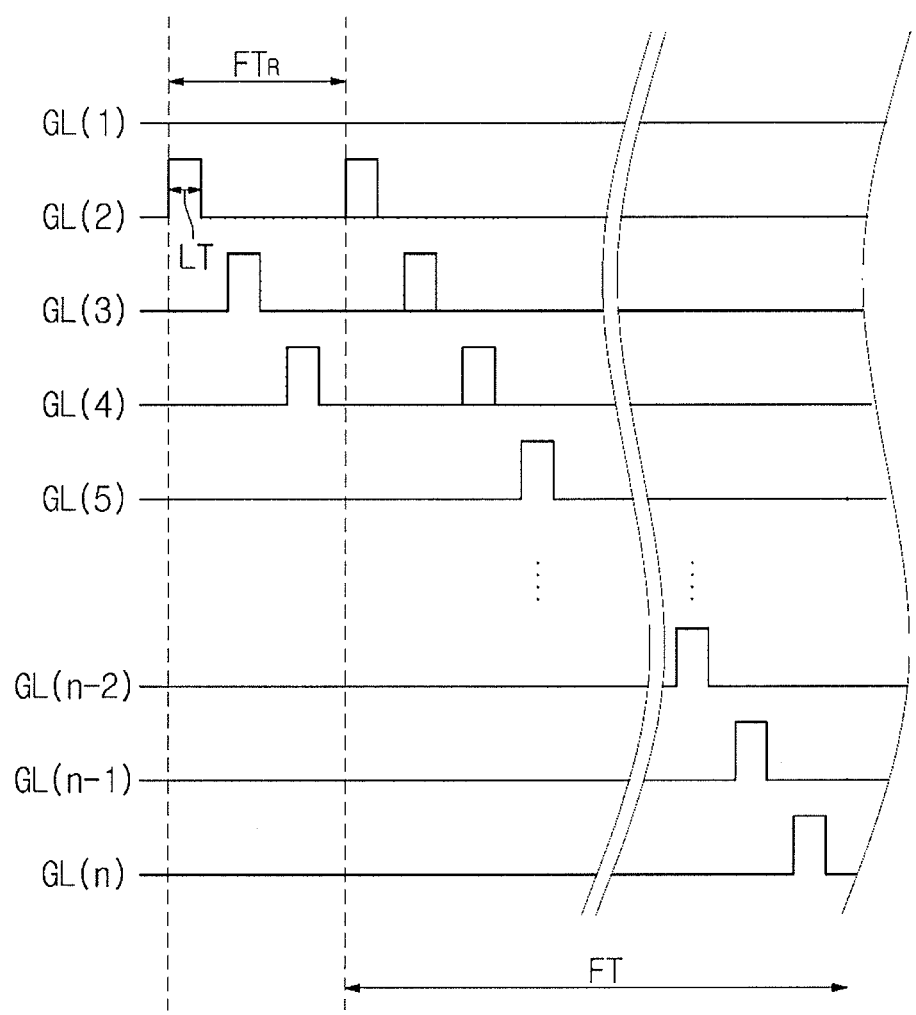
FIG. 4B is a timing diagram illustrating an operation of obtaining an electrical signal by applying different read-out rates for each region.

FIG. 4A is a timing diagram illustrating an operation of obtaining an electrical signal at the same read-out rate for all pixels. FIG. 4B is a timing diagram illustrating an operation of obtaining an electrical signal by applying different read-out rates for each region.

According to an exemplary embodiment, the read-out rate is a factor for indicating a rate of obtaining a frame image in the X-ray detector and uses the number of frame images obtained per second as a unit. According to an exemplary embodiment, the read-out rate indicates a rate at which pixel data is read out, in other words, a rate at which an electrical signal is read out from pixels included in an entire image frame, and a particular read-out rate can be applied to all of the pixels in the image frame, or may be applied to only pixels included in a region or portion (e.g., ROI) of the entire image frame. Further, according to an exemplary embodiment, the term "image frame" or "frame image" may refer to an entire image frame of an image, or may refer to only an image frame of a region or portion (e.g., ROI). In the field of X-ray video, it is possible to obtain the frame image at various different rates, such as, for example, the rates of 5 fps, 10 fps, 15 fps, 20 fps, and 30 fps. In the related art, the same read-out rate is applied to all pixels.

As illustrated in FIG. 4A, when the electrical signal is read out by applying the same read-out rate to all n×m pixels, the gate signal is sequentially applied from a first gate line GL(1) to an n-th gate line GL(n). Therefore, the frame time (FT), which is a time for obtaining a single frame image from all pixels, is determined by a line time (LT), which is a time for applying a gate signal per line, and the number (n) of lines. According to an exemplary embodiment, the line refers to the row.

As described above, the X-ray detector 100 according to an exemplary embodiment may independently read out the electrical signal for each pixel. When the electrical signal is read out only on the ROI, the on signal needs to be applied to only the gate line corresponding to the ROI as illustrated in FIG. 4B. Accordingly, it is possible to obtain the frame image of the ROI within a time shorter than the frame time.

For example, when the frame image of the ROI needs to be obtained at a rate two times faster than that of the frame image of the background, a line scan on the background is performed once while a line scan on the ROI is performed twice as illustrated in FIG. 4B. That is, while two frame images of the ROI are obtained, one frame image of the background is obtained. Although not shown, it should be understood that a gate signal may be applied to the gate line GL(1) if the background area includes the GL(1), and the point of time for applying a gate signal to GL(1) may be before or after a gate signal is applied to an interest area (e.g., ROI). The time for applying a gate signal to GL(1) is not limited to any particular time.

When the frame image of the background is obtained at the same read-out rate as in the frame image of the ROI, since an X-ray dose to be used for obtaining two frame images is accumulated and is used to obtain one frame image, quality of the image increases.

When the ROI is the same as in the above example of FIG. 2, the gate signal needs to be sequentially applied to only GL(2), GL(3), and GL(4). Thereby, a frame time for the ROI (FTR) which is taken for obtaining one frame image of the ROI is reduced to 3/n of a time (FT) taken for obtaining a frame image of an entire region. Also, according to exemplary embodiments, the gate signal supplied to gates during the obtaining of the frame image of the ROI (e.g., gates GL(2), GL(3) and GL(4)) may be supplied at the same sequential rate or a different sequential rate as the gate signal supplied to gates during the obtaining of the frame image of the background (e.g., gates GL(1)-GL(n)).

FIG. 5 is another timing diagram illustrating an operation of obtaining an electrical signal of the X-ray detector according to an exemplary embodiment. The timing diagram of FIG. 5 represents any time point at which a frame image is obtained.

In the above described example of FIG. 4B, a case in which the frame image of the ROI is obtained at a rate two times faster than a rate at which the frame image of the background is obtained was exemplarily described. However, in FIG. 5, a case in which the frame image of the ROI is obtained at a rate of 30 fps and the frame image of the background is obtained at a rate of 5 fps will be exemplarily described.

In this case, 30 frame images of the ROI are obtained per second and 5 frame images of the background are obtained per second. Accordingly, as illustrated in FIG. 5, during 0.2 seconds in which one frame image of the background is obtained, 6 frame images of the ROI may be obtained.

As described above, the X-ray detector 100 can secure a high-quality image such that the frame image of the ROI is obtained at a high read-out rate and thereby movement occurring inside the ROI can be detected more precisely, and the frame image of the background having relatively low importance in movement detection is obtained at a low read-out rate. According to an exemplary embodiment, the high and low read-out rates are high and low relative to each other and are not limited to any particular values.

As will be described below, the X-ray imaging apparatus may enable low-dose X-rays to be incident on the background in order to reduce X-ray exposure to the object. Image quality of the background on which low-dose X-rays are incident may decrease. However, when the X-ray detector 100 obtains the frame image of the background at a low read-out rate, it is possible to restore the image quality according to exemplary embodiments.

Specifically, when the X-ray detector 100 obtains the frame image of the background at a low read-out rate, the first switching element 113 or the second switching element 140 in the pixel corresponding to the background is turned on at a frequency lower than a frequency in the pixel corresponding to the ROI. As a result, a cycle of signal read-out increases and an electric charge accumulation amount increases by an increased cycle. Accordingly, even when low-dose X-rays are incident on the background, it is possible to decrease degradation in the image quality.

Figure 6:
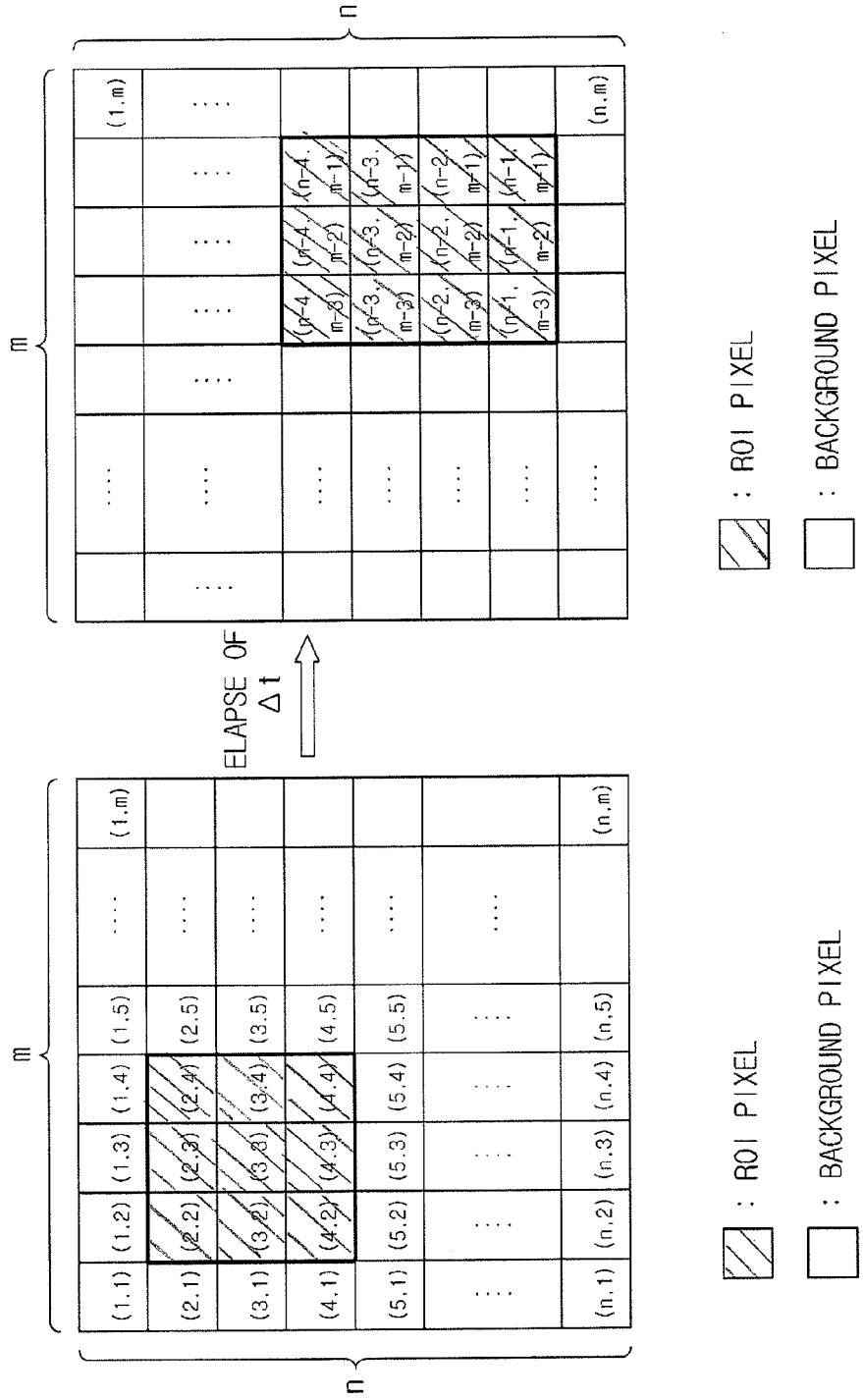
FIG. 6 is a diagram schematically illustrating a position and a size of a region of interest (ROI) that is changing over time.
Figure 7:
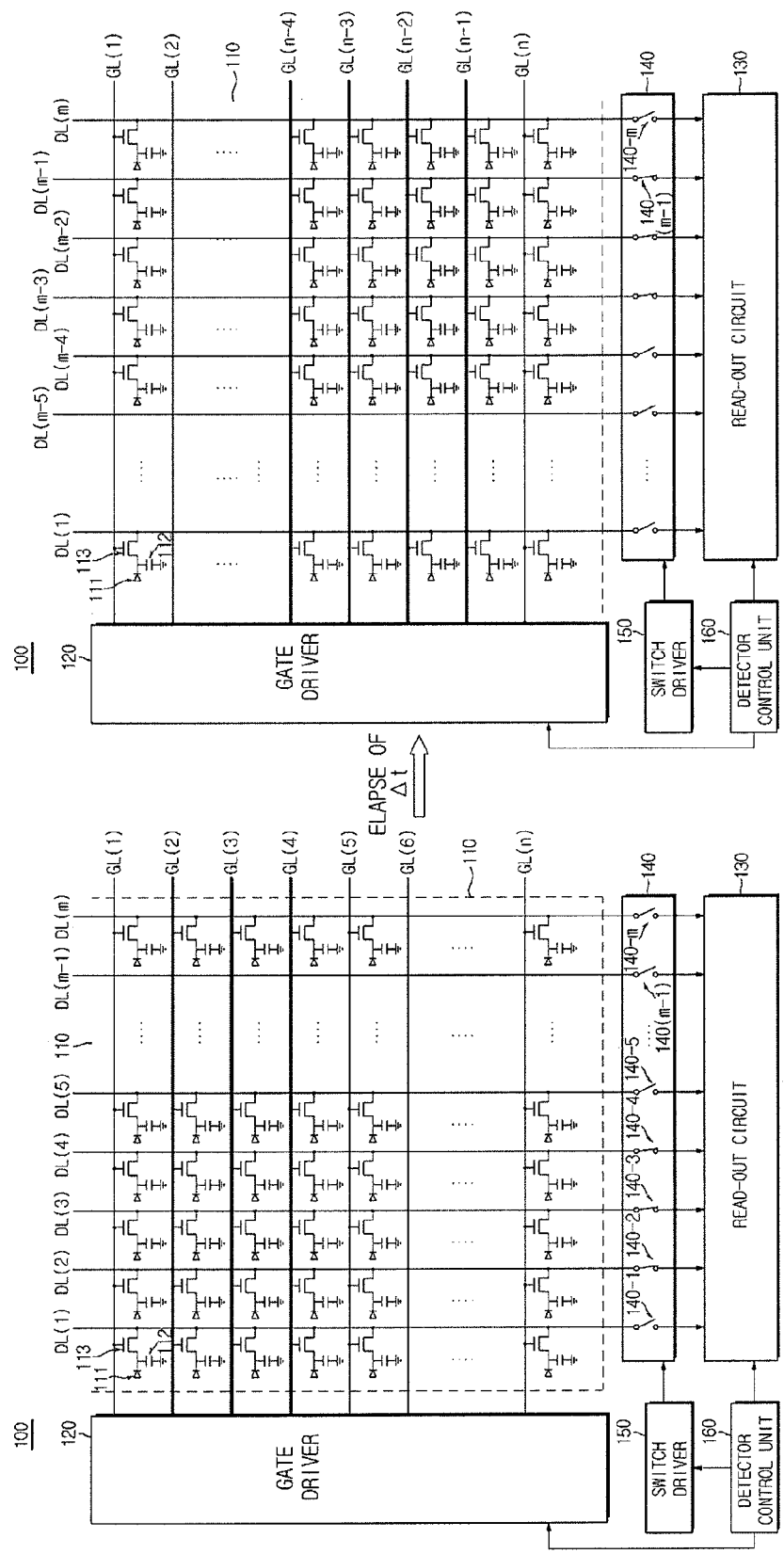
FIG. 7 is a diagram schematically illustrating a change of on and off states of elements of the X-ray detector according to a change of the position and the size of the ROI.

FIG. 6 is a diagram schematically illustrating a position and a size of an ROI that is changing over time. FIG. 7 is a diagram schematically illustrating a change of on and off states of elements of the X-ray detector according to a change of the position and the size of the ROI.

While the X-ray video imaging is performed, a position and a size of the ROI may change over time as illustrated in (a) and (b) of FIG. 6. For example, when the X-ray detector 100 is used for angiography and the ROI is a region including an instrument inserted into a blood vessel, the position and the size of the ROI may change according to movement of the instrument inside the blood vessel.

According to the example of FIG. 6, an ROI having a size of 3×3 and corresponding to pixels in positions (2,2), (2,3), (2,4), (3,2), (3,3), (3,4), (4,2), (4,3), and (4,4) may have a size of 4×3 and correspond to pixels in positions (n−4, m−3), (n−4, m−2), (n−4, m−1), (n−3, m−3), (n−3, m−2), (n−3, m−1), (n−2, m−3), (n−2, m−2), (n−2, m−1), (n−1, m−3), (n−1, m−2), and (n−1, m−1) after a time Δt elapses.

The X-ray detector 100 may obtain the frame image by reflecting a change of the position and the size of the ROI over time. As illustrated in (a) of FIG. 7, when the ROI is the same as (a) of FIG. 6, the on signal is sequentially applied to GL(2), GL(3), and GL(4), and the second switching elements 140-2, 140-3, and 140-4 connected to each of DL(2), DL(3), and DL(4)W are closed.

Then, after a time Δt elapses, when the ROI moves to a position shown in (b) of FIG. 6, the on signal is sequentially applied to GL(n−4), GL(n−3), GL(n−2), and GL(n−1), and the second switching elements connected to DL(m−3), DL(m−2), and DL(m−1) are closed as shown in (b) of FIG. 7.

In the above description, the detector control unit 160 controls the gate driver 120 and the switch driver 150. The detector control unit 160 receives information on the ROI from the image processing unit outside the X-ray detector 100 and controls the gate driver 120 and the switch driver 150 such that the on signal is applied to the gate line and the second switching element, which correspond to the ROI.

Specifically, the detector control unit 160 selects the gate line and the second switching element, which correspond to the ROI, and controls a timing of the on signal applied to the selected gate line and second switching element. At this time, the detector control unit 160 may synchronize a timing of the on signal applied to the second switching element with a timing of the on signal applied to the gate line.

The timing of the on signal may be changed according to the read-out rates applied to the ROI and the background. The read-out rate applied to each region may be set in the detector control unit 160, set in the control unit included in the X-ray imaging apparatus, or set by the user.

When the detector control unit 160 or the control unit included in the X-ray imaging apparatus sets the read-out rate, it is possible to set the read-out rate to be applied to the ROI by reflecting a movement characteristic inside the ROI and the read-out rate to be applied to the background by reflecting the X-ray dose incident on the background.

Specifically, as the movement inside the ROI becomes greater, the read-out rate to be applied to the ROI may be set to be higher, and as the X-ray dose incident on the background becomes lower, the read-out rate to be applied to the background may be set to be lower.

Referring again to FIG. 3, the detector control unit 160 receives the information on the ROI, selects GL(2), GL(3), and GL(4) as the gate lines corresponding to the ROI, and selects the second switching elements 140-2, 140-3, and 140-4 connected to DL(2), DL(3), and DL(4) as the second switching elements corresponding to the ROI.

In order to obtain the frame image of the ROI, the detector control unit 160 applies the on signal to the GL(2), and applies the on signal to the second switching elements 140-2, 140-3, and 140-4 connected to DL(2), DL(3), and DL(4). The detector control unit 160 may simultaneously apply the on signal to the second switching elements and GL(2), or may apply these signals at different times. According to an exemplary embodiment, the detector control unit 160 applying a signal refers to controlling the gate driver 120 and the switch driver 150 such that the signal is applied.

When applying of the on signal to GL(2) is completed, the on signal is applied to GL(3), and the on signal may be applied to the second switching elements 140-2, 140-3, and 140-4 connected to DL(2), DL(3), and DL(4) at the same time.

When applying of the on signal to GL(3) is completed, the on signal is applied to GL(4), and the on signal may be applied to the second switching elements 140-2, 140-3, and 140-4 connected to DL(2), DL(3), and DL(4) at the same time.

On the other hand, the on signal applied to each of the second switching elements may also be applied at the same time. Further, according to a characteristic of elements constituting the X-ray detector 100, the on signal may also be sequentially applied from a second switching element corresponding to a pixel at which the gate signal arrives first.

In addition, with respect to the gate signal and the on signal of the second switching element, according to a characteristic of elements constituting the X-ray detector 100, the on signal may be applied to the second switching element after the gate signal is applied.

Hereinafter, an exemplary embodiment of the X-ray imaging apparatus including the X-ray detector will be described.

Figure 8:
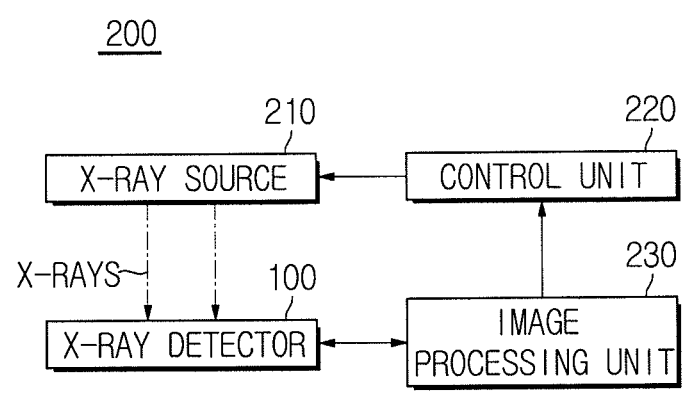
FIG. 8 is a control block diagram illustrating an X-ray imaging apparatus according to an exemplary embodiment.
Figure 9:
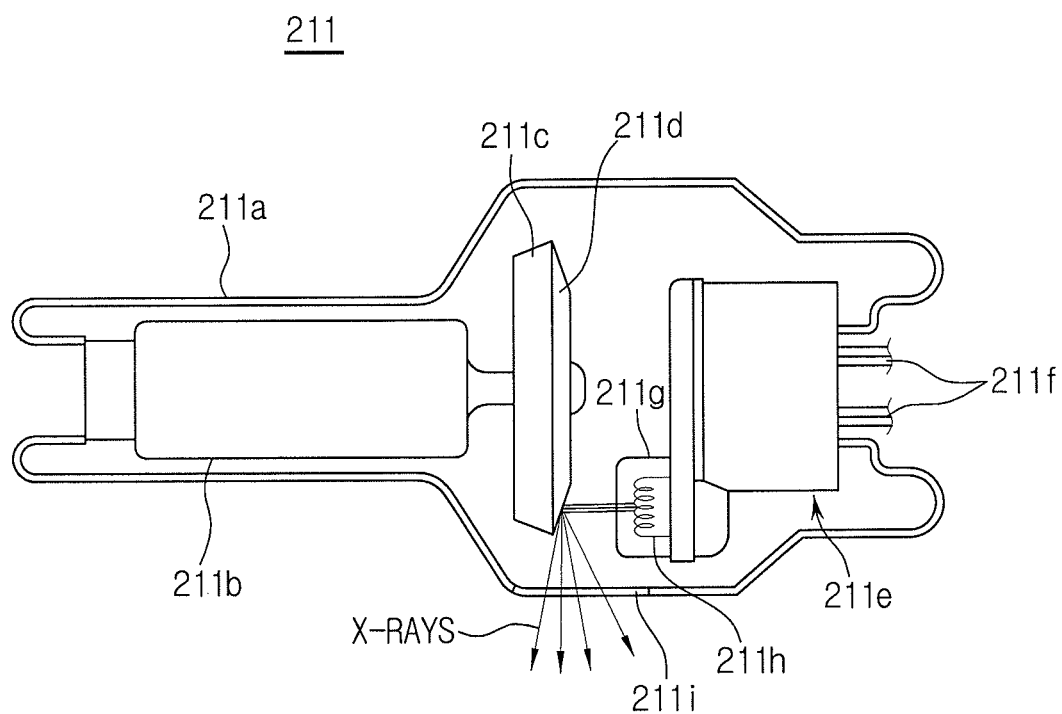
FIG. 9 is a cross-sectional view illustrating a configuration of an X-ray tube included in the X-ray imaging apparatus according to an exemplary embodiment.

FIG. 8 is a control block diagram illustrating an X-ray imaging apparatus according to an exemplary embodiment. FIG. 9 is a cross-sectional view illustrating a configuration of an X-ray tube included in the X-ray imaging apparatus according to an exemplary embodiment.

As illustrated in FIG. 8, an X-ray imaging apparatus 200 according to an exemplary embodiment includes an X-ray source 210 configured to generate and radiate X-rays, the X-ray detector 100 configured to obtain a frame image by detecting the radiated X-rays, an image processing unit 230 (e.g., image processor) configured to obtain information on the ROI from the frame image, and a control unit 220 (e.g., controller) configured to control the X-ray source 210.

As illustrated in FIG. 9, the X-ray source 210 may include an X-ray tube 211 configured to generate X-rays. An anode 211c and a cathode 211e are provided in a glass tube 211a of the X-ray tube 211. An inside of the glass tube 211a is maintained in a high vacuum state and thermoelectrons are generated by heating a filament 211h of the cathode 211e. The filament 211h may be heated by applying a current to an electrical conductor 211f connected to the filament.

The cathode 211e includes the filament 211h and a focusing electrode 211g configured to focus electrons. The focusing electrode 211g is also called a focusing cup.

When a high voltage is applied between the anode 211c and the cathode 211e, thermoelectrons are accelerated and collide with a target material 211d of the anode 211c, and thereby X-rays are generated. High-resistance materials such as Cr, Fe, Co, Ni, W, and Mo may be used as the target material 211d of the anode. The generated X-rays are radiated to the outside through a window 211i, and a beryllium (Be) film may be used as a material of the window.

The voltage applied between the anode 211c and the cathode 211e is referred to as a tube voltage and a level thereof may be indicated as peak kilovoltage (kVp). As the tube voltage increases, a rate of thermoelectrons increases. As a result, energy (photon energy) generated by the X-rays colliding with the target material 211d increases. In addition, a filter is disposed in a radiation direction of X-rays and thereby energy of the X-rays may also be adjusted. A filter configured to filter X-rays of a specific wavelength band may be positioned in front of or behind the window 211i, and thereby it is possible to filter X-rays of a specific wavelength band. For example, when a filter made of aluminum or copper is provided, X-rays of a low-energy band are filtered and energy of radiating X-rays increases.

A current flowing in the X-ray tube 211 is referred to as a tube current and may be indicated as an average mA. As the tube current increases, the X-ray dose (the number of X-ray photons) increases. Therefore, the energy of the X-rays may be controlled by the tube voltage, and the X-ray dose may be controlled by the tube current and an X-ray exposure time.

The X-ray imaging apparatus 200 according to an exemplary embodiment may be applied in various fields of X-ray diagnosis, such as fluoroscopy and angiography, or fields of various operations using the same, and thereby, an X-ray video may be generated. The X-ray video may be generated and displayed in real time.

The X-ray imaging apparatus 200 consecutively performs X-ray imaging in order to generate the X-ray video. A method of consecutively performing X-ray imaging includes a continuous exposure method and a pulse exposure method.

When the continuous exposure method is applied, a low tube current is continuously supplied to the X-ray tube 211 and thereby X-rays are continuously generated. When the pulse exposure method is applied, X-rays are generated by successive short pulses. The X-ray imaging apparatus 200 may apply any of the two methods, or other methods known to those skilled in the art.

According to an exemplary embodiment, the object may refer to an X-ray imaging target, that is, a target of which an inside should be represented as an X-ray image, and an object region may refer to a specific region including the object and may also refer to a region to be imaged as an X-ray image. Accordingly, the object region may match a field of view (FOV) of the X-ray imaging apparatus 200.

The object region may include at least one of the ROI and the background. A region other than the ROI in the object region is the background. The ROI and the background will be described in detail below.

Referring again to FIG. 8, the X-ray detector 100 detects X-rays and obtains a plurality of frame images of the object region, and may have the same configuration as the X-ray detector according to the exemplary embodiments described above with reference to FIGS. 1 to 7.

The image processing unit 230 analyzes the frame image of the object region and obtains information on the ROI. Analysis of the frame image will be described in detail below.

The control unit 220 may control the X-ray source 210. For this purpose, the control unit 220 may receive information on the ROI from the image processing unit 230 and determine parameters for controlling the X-ray source 210 based on the information on the ROI.

Also, the function of the detector control unit 160 described in the above exemplary embodiment may also be performed by the control unit 220. For example, when it is difficult to integrate the detector control unit 160 into the X-ray detector 100, the X-ray detector 100 does not include the detector control unit 160 and the control unit 220 may perform the same function.

As described above, the X-ray imaging apparatus 200 may consecutively perform X-ray imaging and obtain the X-ray video on the object region. The frame images obtained by the X-ray detector 100 are input to the image processing unit 230, and the image processing unit 230 may analyze the input frame images and obtain information on the ROI.

First, the image processing unit 230 detects an object of interest from the frame image of the object region. In order to detect the object of interest, a characteristic of the object of interest is previously stored and an object corresponding to the pre-stored characteristic is detected from the frame image of the object region. For example, characteristics of the object of interest may include characteristics such as a shape, an X-ray absorption characteristic, and a movement characteristic of the object of interest, and at least one of these and/or other types of characteristics that can be detected from the X-ray image may be stored in advance.

The object of interest may refer to an object that the user continuously watches while X-ray imaging is performed and may be the instrument inserted into the object or an operation site. For example, if the X-ray imaging apparatus 200 is used for angiography, when the instrument such as a guide wire, a catheter, a needle, a balloon, or a stent is inserted into the blood vessel, careful observation of the instrument may be necessary. Therefore, the instrument may be set as the object of interest and information on a characteristic thereof may be stored in advance.

Also, when the operation site is set as the object of interest, a region of stenosis or aneurysm, a cancerous region, or other types of regions may be set as the object of interest.

When the object of interest is detected, the image processing unit 230 sets a specific region including the detected object of interest as the ROI. The position and the size of the ROI may be determined in consideration of the position and the size of the object of interest or the movement characteristic of the object of interest.

Figure 10:
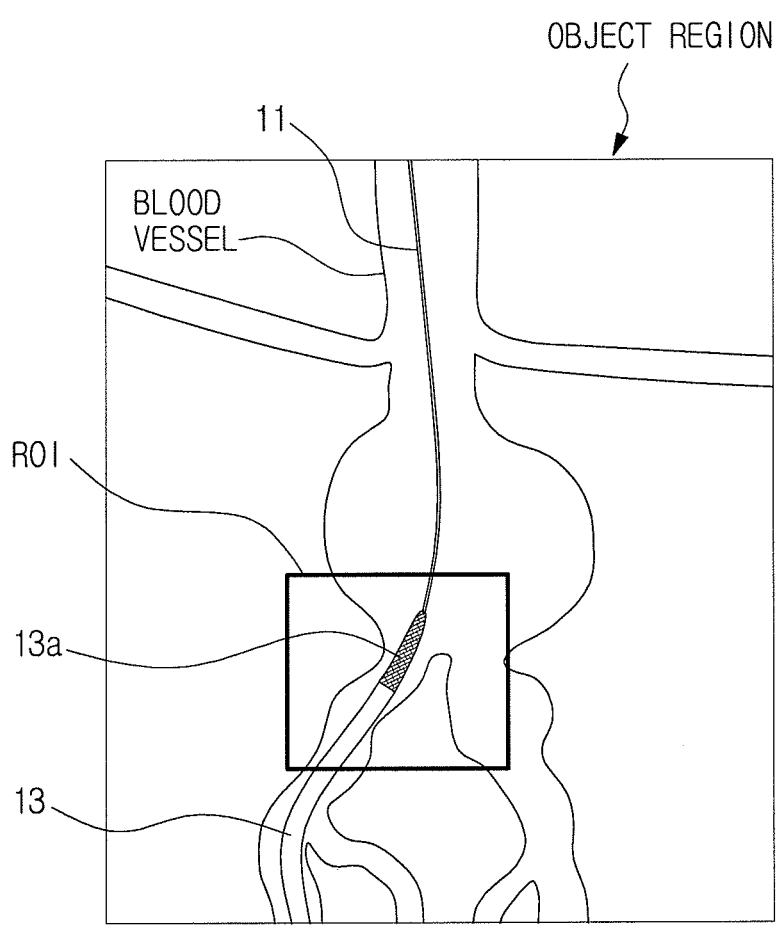
FIG. 10 is a diagram schematically illustrating an exemplary ROI that can be set in the X-ray imaging apparatus according to an exemplary embodiment.

FIG. 10 is a diagram schematically illustrating an exemplary ROI that can be set in the X-ray imaging apparatus according to an exemplary embodiment.

FIG. 10 exemplifies a case in which a stent is inserted into a blood vessel using angiography. A stent 13a is inserted into the blood vessel in order to prevent obstruction of the blood vessel and the like, and has a mesh shape. The stent 13a is folded and inserted into an end of a stent device 13 having a long tube shape, is introduced into the blood vessel, and is spread at a desired position in a mesh shape.

As illustrated in FIG. 10, in order to insert the stent device 13 into the blood vessel of the object region, a guide wire 11 is inserted first. The stent device 13 is inserted into the blood vessel along the guide wire 11. While the stent device 13 is inserted, the stent device 13, and specifically, the tip of the stent 13a, may be the object of interest, and a specific region including the stent 13a may become the ROI.

While the guide wire 11 is inserted, the guide wire 11 or a tip of the guide wire 11 may be the object of interest. While the catheter is inserted into the blood vessel in order to inject a contrast agent, the catheter or a tip of the catheter may be the object of interest.

Alternatively, the image processing unit 230 may also use information input from the outside to detect the object of interest. For example, information on a type of the instrument, a type of the operation, the operation site, and injection of the contrast agent may be input, and it may therefore be possible to detect the object of interest from the frame image based on the input information.

For example, when information that an operation to be performed is an aortic stenting procedure and an instrument to be inserted is a stent device is input, the image processing unit 230 uses the pre-stored information on the characteristic of the stent and detects the stent inside the aorta from the frame image of the object region.

The image processing unit 230 may determine the movement characteristic of the object of interest while tracking the detected object of interest. Detecting and tracking of the object of interest, and obtaining information on the ROI, may be performed in real time according to the read-out rate of the frame images input to the image processing unit 230. According to an exemplary embodiment, obtaining the information on the ROI includes detecting and tracking the object of interest and setting the ROI based on the result thereof.

The movement characteristic of the object of interest may include information on a movement size, a movement direction, and the like of the object of interest. The movement size may include a speed, although the movement of the object of interest may have no constant pattern. Therefore, the movement size may include various pieces of information indicating a movement degree in addition to the speed.

The ROI is a specific region including the object of interest and is defined by the object of interest. Therefore, the movement characteristic of the ROI may be determined according to the movement characteristic of the object of interest.

Also, information on the ROI obtained by the image processing unit 230, and specifically, information on the position, the size, or the movement characteristic of the ROI, is transmitted to the X-ray detector 100 and used to control obtaining of the frame image.

Also, in addition to the information on the ROI, the image processing unit 230 may obtain information on image characteristics represented in the frame image such as noise and contrast. These characteristics may be transmitted to the control unit 220 and used to control X-ray imaging conditions.

The control unit 220 controls various imaging parameters applied to X-ray imaging. The imaging parameter may also be referred to as an exposure parameter. Automatically controlling the imaging parameter in the X-ray imaging apparatus 200 may be referred to as auto exposure control.

The imaging parameter may be at least one selected from the group including the tube voltage, the tube current, the exposure time, a type of the filter, the FOV, the read-out rate, the pulse rate, and a type of the target material.

The imaging parameter may be determined based on the frame image of the object region and may also be determined based on previous information input before X-ray imaging begins. Hereinafter, an exemplary embodiment of the former case will be described in detail.

The control unit 220 may determine the imaging parameter based on an analysis result of the image processing unit 230. For example, when the image processing unit 230 analyzes the frame image and determines characteristics such as a thickness or a density of the object, the control unit 220 may determine the imaging parameter such as the tube voltage, the tube current, the exposure time, a type of the filter, and a type of the target material, which matches the characteristic of the object, based on the analysis result.

In addition, the control unit 220 may also determine the imaging parameter based on the information on the ROI obtained by the image processing unit 230. For example, according to the movement size of the object of interest or image characteristics represented in the ROI, the control unit 220 may determine and control the imaging parameter such as the read-out rate, the tube current, and a dose per frame to be applied to the ROI.

For example, the control unit 220 sets the read-out rate to be applied to the ROI to be higher as the movement size of the object of interest increases, and thereby the movement of the object of interest may be detected more precisely. Information on the set read-out rate is delivered to the X-ray detector 100.

Also, the control unit 220 may also control the dose per frame according to a noise level of the ROI, that is, control the exposure time and the tube current supplied to the X-ray tube 211. For example, when the noise level of the ROI is greater than a predetermined reference value, the dose per frame increases and thereby the noise level decreases, and on the other hand, when the noise level of the ROI is lower than a predetermined reference value, the dose per frame decreases and thereby exposure to the object may decrease.

The control unit 220 may also set the read-out rate to be applied to the background. In consideration of the dose per frame and a filtering rate of an ROI filter 241, the X-ray dose to be incident on the background is estimated and the read-out rate to be applied to the background may be set based on the X-ray dose to be incident on the background. Specifically, the lower the X-ray dose incident on the background, the lower a read-out rate may be set.

Figure 11:
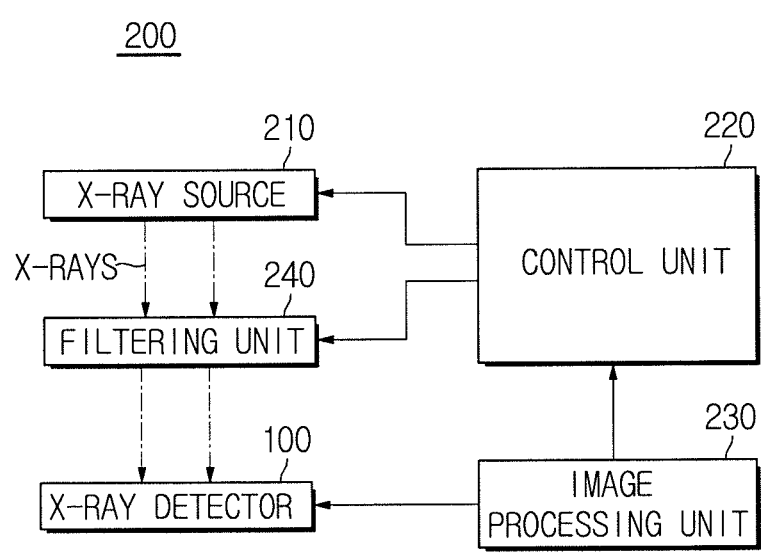
FIG. 11 is a control block diagram of an X-ray imaging apparatus further including a filtering unit according to an exemplary embodiment.
Figure 12:
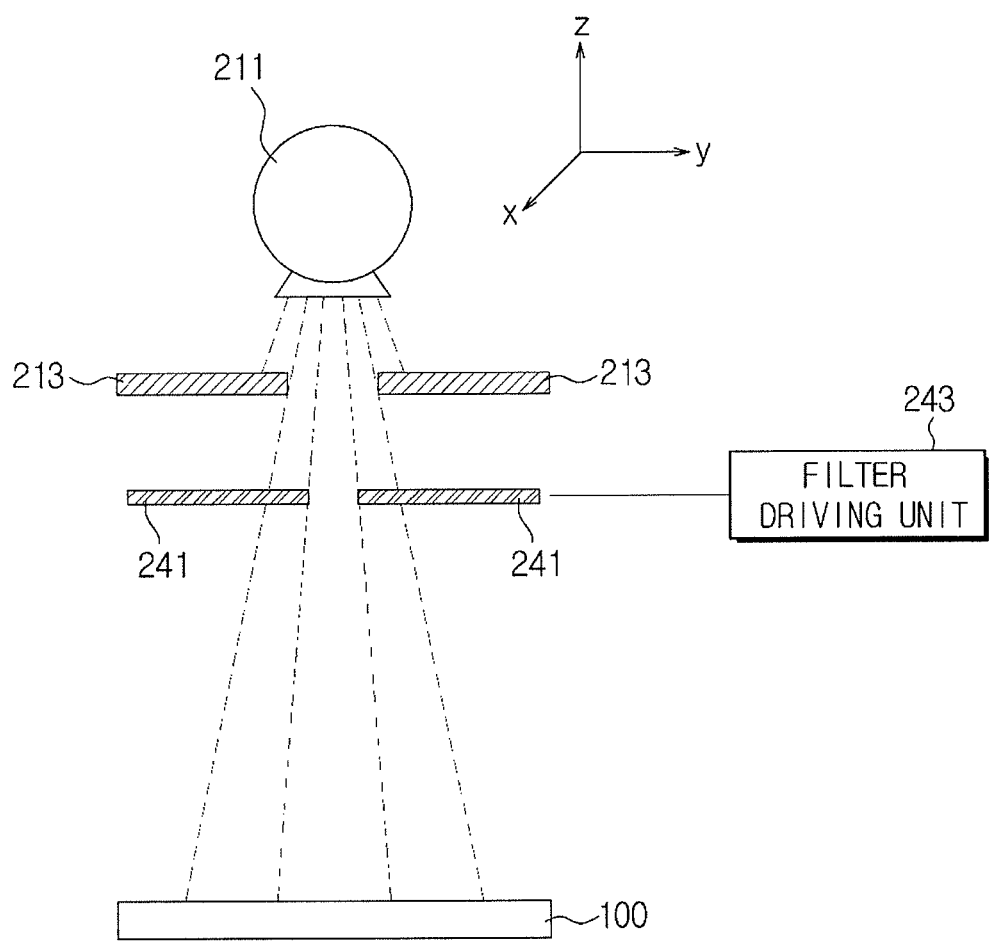
FIG. 12 is a cross-sectional side view of an ROI filter included in the filtering unit.

FIG. 11 is a control block diagram of an X-ray imaging apparatus further including a filtering unit according to an exemplary embodiment. FIG. 12 is a cross-sectional side view of an ROI filter included in the filtering unit.

As illustrated in FIG. 11, the X-ray imaging apparatus 200 according to an exemplary embodiment may further include a filtering unit 240 (e.g., filter) configured to filter X-rays radiated from the X-ray source 210.

The filtering unit 240 filters X-rays radiated from the X-ray source 210 and enables X-rays having a dose lower than a dose of X-rays incident on the ROI to be incident on a non-ROI. This operation is performed to reduce X-ray exposure to the object. Through the X-ray filtering, X-rays having a dose relatively higher than a dose of X-rays incident on the non-ROI are applied to the ROI in which much useful information on the inside of the object is included, and X-rays having a dose lower than a dose of the X-rays incident on the ROI are applied to the non-ROI in which a small amount of information is included.

As illustrated in FIG. 12, the filtering unit 240 includes the ROI filter 241 and a filter driving unit 243 (e.g., filter driver) configured to move the ROI filter 241. The filter driving unit 243 may include a mechanical structure such as a motor configured to generate power and a gear configured to deliver the generated power to the ROI filter 241.

The ROI filter 241 may move in a 3D space defined by x, y, and z axes by the filter driving unit 243, and specifically, may move on an x-y plane or along the z axis. Movement on the x-y plane is performed in order to enable the position of the background to correspond to the ROI filter 241. Movement along the z axis is performed in order to enable the size of the ROI to correspond to the ROI filter 241.

A collimator 213 may be disposed in front of the X-ray tube 211, that is, in a position near which X-rays are radiated by the X-ray tube 211. The collimator 213 is made of a material that absorbs or blocks X-rays such as lead or tungsten, adjusts an X-ray radiating region of the X-ray source 210, that is, a range of the FOV, and reduces X-ray scattering.

The ROI filter 241 is positioned between the collimator 213 and the X-ray detector 100, and may filter X-rays radiated from the X-ray source 210. The ROI filter 241 may be made of a material that reduces X-rays. The X-rays decrease and a dose thereof decreases while passing the ROI filter 241. Accordingly, when the ROI filter 241 is positioned at a position corresponding to the background of the object region, X-rays having a dose lower than a dose of X-rays incident on the ROI may be incident on the background.

In general, since the ROI is surrounded by the background, the ROI filter 241 may have a shape having an empty center, that is, a ring shape in which an opening is formed at a center.

The control unit 220 generates a control signal for moving the ROI filter 241 based on information on the ROI, transmits the generated control signal to the filter driving unit 243, and may move the ROI filter 241 to a position corresponding to the background. When the ROI filter 241 moves to the position corresponding to the background, X-rays incident on the background are filtered by the ROI filter 241, and X-rays passing the opening of the ROI filter 241 are incident on the ROI.

Specifically, the control unit 220 may control movement on the x-y plane of the ROI filter 241 such that the opening of the ROI filter 241 is positioned at the position corresponding to the ROI, and control movement along the z axis of the ROI filter 241 such that the opening of the ROI filter 241 corresponds to the size of the ROI.

When the X-ray tube 211 radiates X-rays in the form of a fan beam or a cone beam, as the ROI filter 241 is moved closer to the X-ray tube 211 or the collimator 213, a width of X-rays incident on the ROI filter 241 decreases, and conversely, as the ROI filter 241 is moved farther away from the X-ray tube 211, a width of X-rays incident on the ROI filter 241 increases. As the width of X-rays incident on the ROI filter 241 increases, a filtering region also increases.

Therefore, in order to increase the ROI by decreasing the filtering region, the ROI filter 241 moves to a side towards the X-ray tube 211 or the collimator 213 along the z axis. In order to decrease the ROI by increasing the filtering region, the ROI filter 241 moves to a side opposite to the X-ray tube 211 or the collimator 213 along the z axis.

However, the ROI filter 241 illustrated in FIG. 12 is only an example that can be applied to exemplary embodiments.

Alternatively, various other types of filter structures capable of reducing the X-ray dose incident on the background may be applied.

Figure 13:
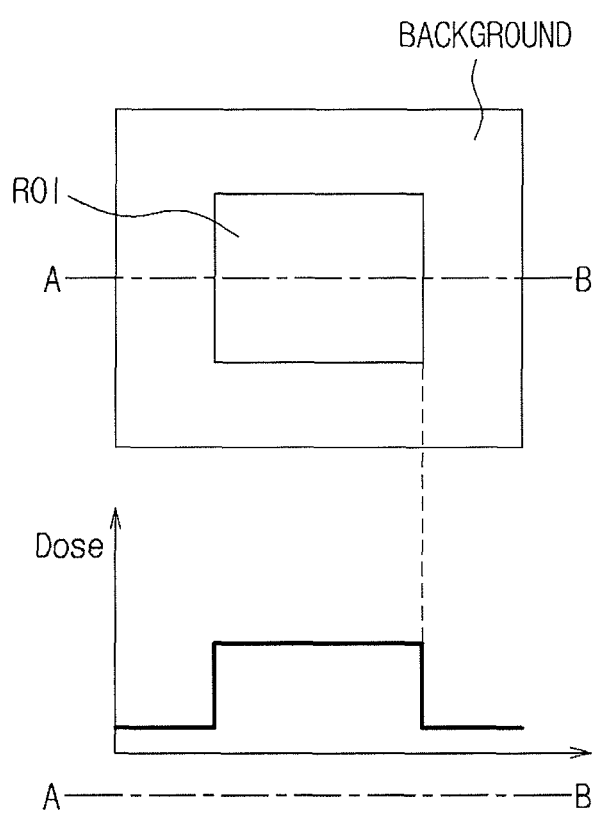
FIG. 13 is a diagram schematically illustrating an X-ray dose incident on the ROI and a background.

FIG. 13 is a diagram schematically illustrating an X-ray dose incident on the ROI and the background.

FIG. 13 illustrates the X-ray dose incident on an arbitrary straight line AB which crosses the ROI and the background. When the control unit 220 moves the ROI filter 241 to the position corresponding to the background, X-rays having a dose lower than a dose of X-rays incident on the ROI are incident on the background as illustrated in FIG. 13. Since low-dose X-rays are incident on the background, it is possible to reduce X-ray exposure to the object.

When low-dose X-rays are incident on the background, a signal-to-noise ratio of the frame image may decrease. However, as described above, since the X-ray detector 100 obtains the frame image of the background at a low read-out rate, it is possible to prevent degradation in image quality of the frame image of the background.

The control unit 220 may set the read-out rate of the frame image of the background in consideration of the X-ray dose incident on the background. Information on the set read-out rate is delivered to the X-ray detector 100.

Figure 15:
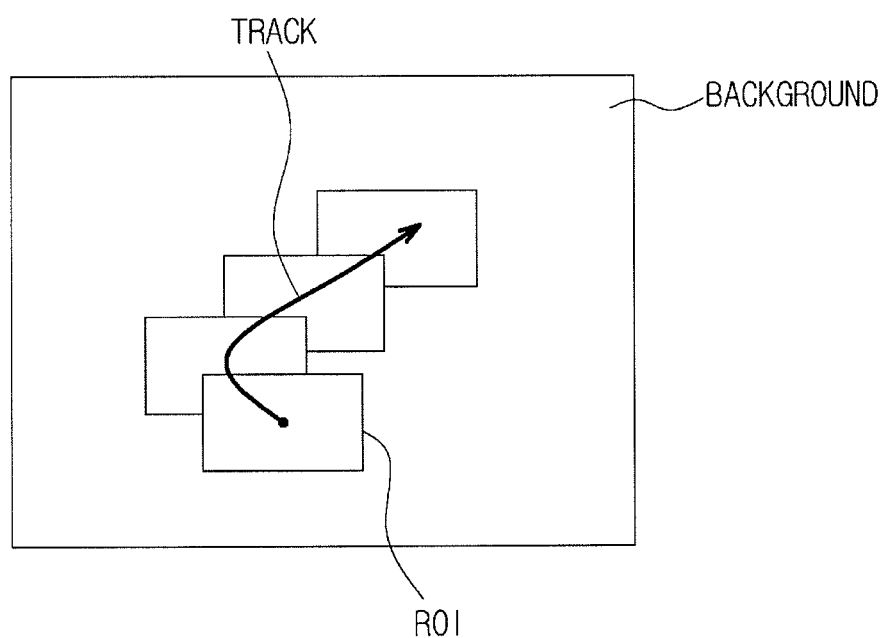
FIG. 15 is a diagram schematically illustrating an operation of tracking a moving ROI.

FIG. 14 is a diagram illustrating movement of the ROI according to movement of the object of interest. FIG. 15 is a diagram schematically illustrating an operation of tracking a moving ROI.

The X-ray video may represent movement in the object region, and when a subject of the movement is the object of interest, the ROI may move according to the movement of the object of interest. For example, as illustrated in (a) and (b) of FIG. 14, when a stent inserting procedure for inserting the stent device 13 into the blood vessel is performed, the stent 13a serving as the object of interest moves to a target position inside the blood vessel, and the ROI also moves according to the movement of the stent 13a.

The image processing unit 230 may perform detecting and tracking of the object of interest in real time. As illustrated in FIG. 15, when the ROI moves, the image processing unit 230 tracks the movement in real time, and the control unit 220 controls the ROI filter 241 to be synchronized with the movement of the ROI and moves the ROI filter 241 and the ROI together.

Also, the X-ray detector 100 receives information on the ROI in real time and controls the read-out rate for each pixel by reflecting the movement of the ROI.

Figure 16:
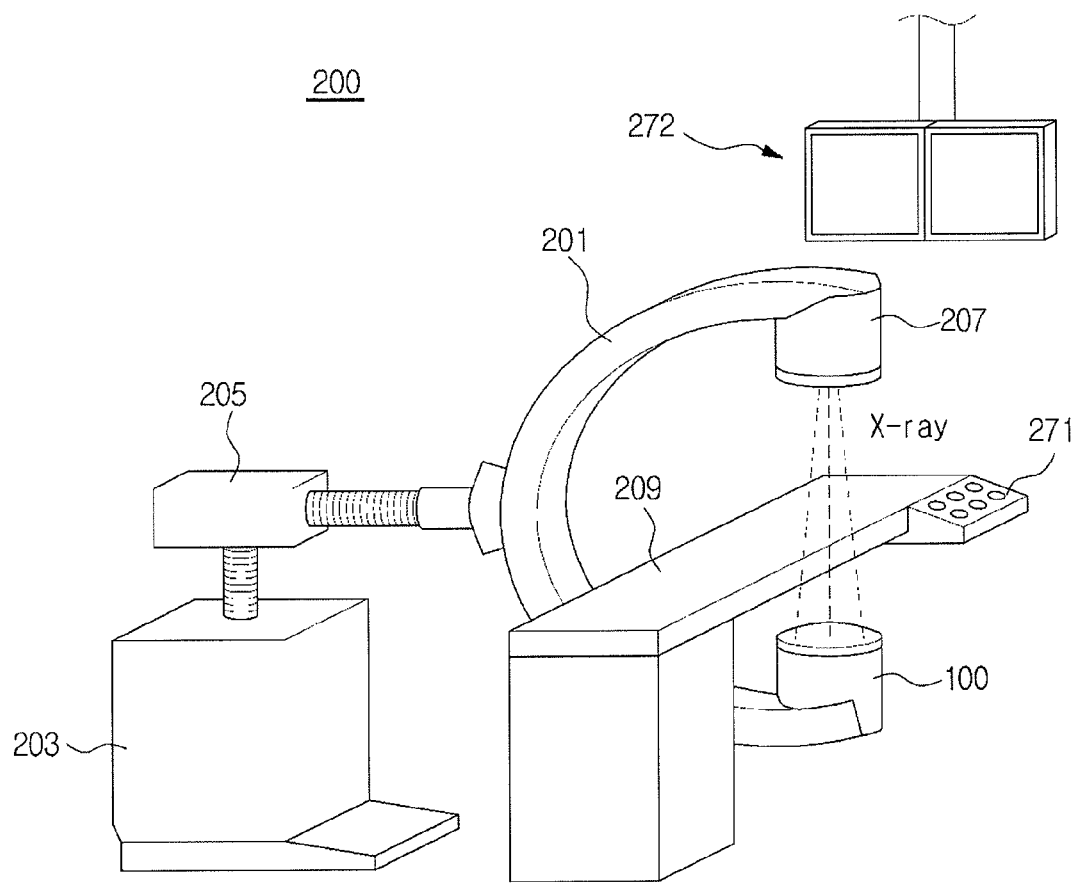
FIG. 16 is a diagram illustrating an appearance of the X-ray imaging apparatus according to an exemplary embodiment.

FIG. 16 is a diagram illustrating an appearance of the X-ray imaging apparatus according to an exemplary embodiment.

For example, as illustrated in FIG. 16, the X-ray imaging apparatus 200 may have a C-arm structure. An X-ray source assembly 207 and the X-ray detector 100 may be provided in each end of a C-arm 201 having a C shape. The C-arm 201 is connected to a main body 203 through a connecting shaft 205 and is rotatable in an orbital direction.

An inside of the X-ray source assembly 207 may include the X-ray tube 211, the collimator 213, and the filtering unit 240. A patient table 209 is positioned between the X-ray source assembly 207 and the X-ray detector 100. When the object is positioned on the patient table 209, the X-ray source 210 radiates X-rays onto the object, the X-ray detector 100 detects X-rays transmitted through the object, and thereby the X-ray image of the object is obtained.

As described above, the X-ray imaging apparatus 200 may obtain the video on the object in real time. The user may perform operations or diagnosis while watching a display unit 272 that has a plurality of screens and can display several images necessary for operations or diagnosis.

As described above, when the image processing unit 230 obtains the information on the ROI or the control unit 220 sets the imaging parameter, information input by the user may be used. The user may input necessary information through an input unit 271 provided in the X-ray imaging apparatus 200.

Hereinafter, an exemplary embodiment of a method of controlling an X-ray detector according to an aspect of an exemplary embodiment will be described.

Figure 17:
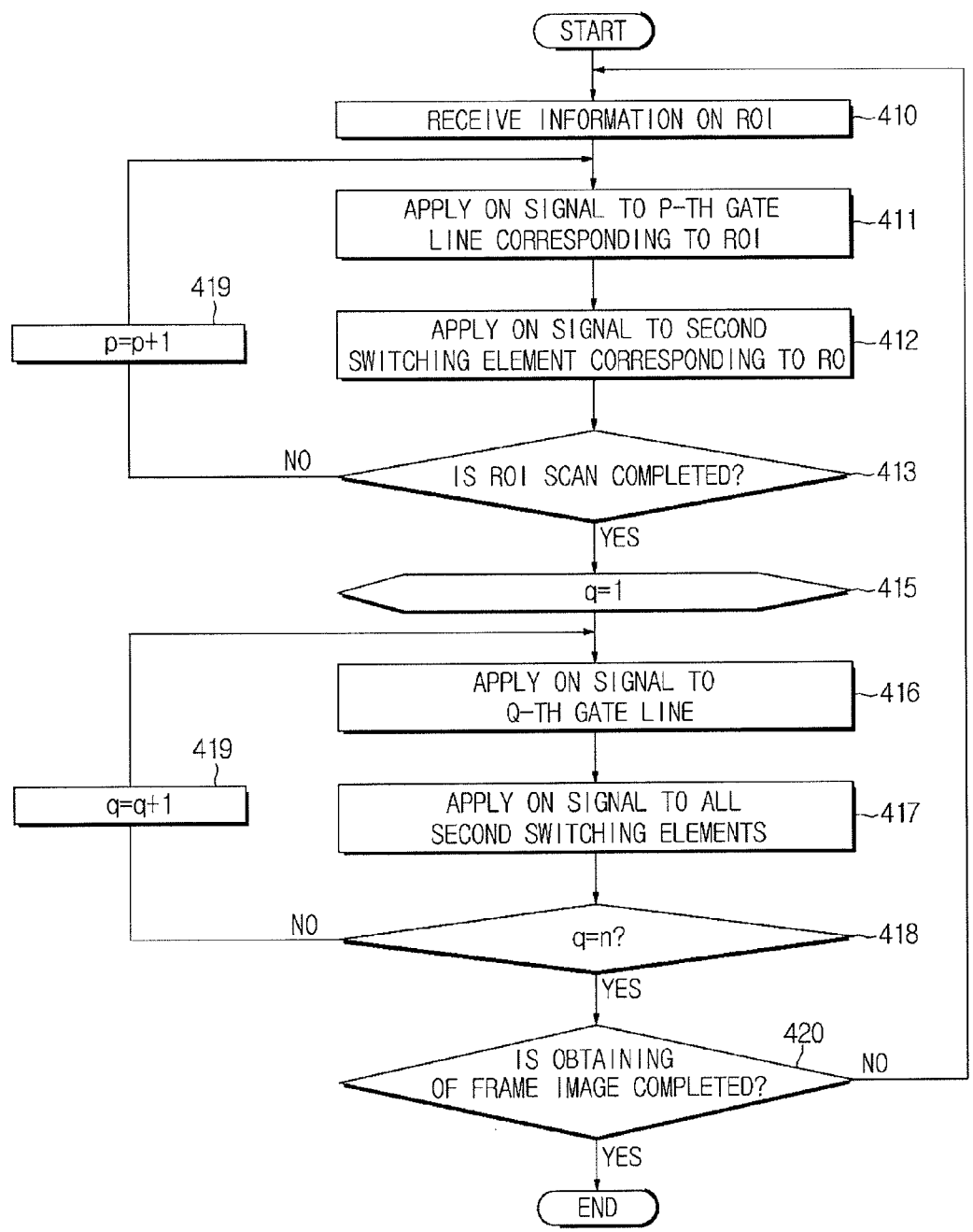
FIG. 17 is a flowchart illustrating a method of controlling an X-ray detector according to an exemplary embodiment.

FIG. 17 is a flowchart illustrating a method of controlling an X-ray detector according to an exemplary embodiment. The X-ray detector 100 according to any one of the aforementioned exemplary embodiments may be applied to the exemplary embodiment and the X-ray detector 100 may include nxm two-dimensionally arranged pixels. Also, the flowchart in FIG. 17 may represent a cycle of electrical signal read-out at any time point while the frame image is obtained.

As illustrated in FIG. 17, information on the ROI is received at operation 410. The information on the ROI may, for example, be obtained by the X-ray imaging apparatus having the X-ray detector and delivered to the X-ray detector. Since the information on the ROI may be received in real time, the position and the size of the ROI may be changed over time.

The read-out rate to be applied to the ROI and the background may be set in the X-ray imaging apparatus and may also be set in the X-ray detector. Hereinafter, in the exemplary embodiment to be described, the read-out rate to be applied to the ROI may be referred to as a first read-out rate, and the read-out rate to be applied to the background may be referred to as a second read-out rate. In this exemplary embodiment, a case in which the first read-out rate is set to twice the second read-out rate will be exemplarily described, although it is understood that the first read-out rate may be more or less than twice the second read-out rate.

The on signal is applied to a p-th gate line corresponding to the ROI at operation 411. When the X-ray detector 100 includes n gate lines, p may be a positive integer equal to or less than n. The gate line corresponding to the ROI refers to a gate line to which a pixel corresponding to the ROI is connected. When any pixel corresponding to the ROI is connected, the gate line of the pixel becomes the gate line corresponding to the ROI.

Then, the on signal is applied to the second switching element corresponding to the ROI at operation 412. The second switching element corresponding to the ROI refers to a second switching element connected to the data line to which the pixel corresponding to the ROI is connected. Applying the on signal to the p-th gate line GL(p) and applying the on signal to the second switching element 140 may be performed at the same time or sequentially performed.

When a scan on the ROI is not completed (No in operation 413), a number of a scan target gate line is increased by one at operation 414, and the on signal is applied to a corresponding gate line and second switching element. These operations are repeated until the scan on the ROI is completed.

When a scan on the ROI is completed (Yes in operation 413), a scan is performed on an entire region including the background and the ROI. Specifically, the on signal is applied to a first gate line (operations 415 and 416), and the on signal is applied to all second switching elements, that is, m second switching elements (operation 417). When the scan is not completed up to an n-th gate line (Yes in operation 418), while a number of a scan target gate line is increased by one at operation 418, the on signal is applied to the gate line and the second switching element.

When obtaining of the frame image is completed (Yes in operation 420), the process ends, and otherwise (No in operation 420), the process is performed beginning from operation 410 again.

Hereinafter, an exemplary embodiment of a method of controlling an X-ray imaging apparatus according to an aspect of an exemplary embodiment will be described.

Figure 18:
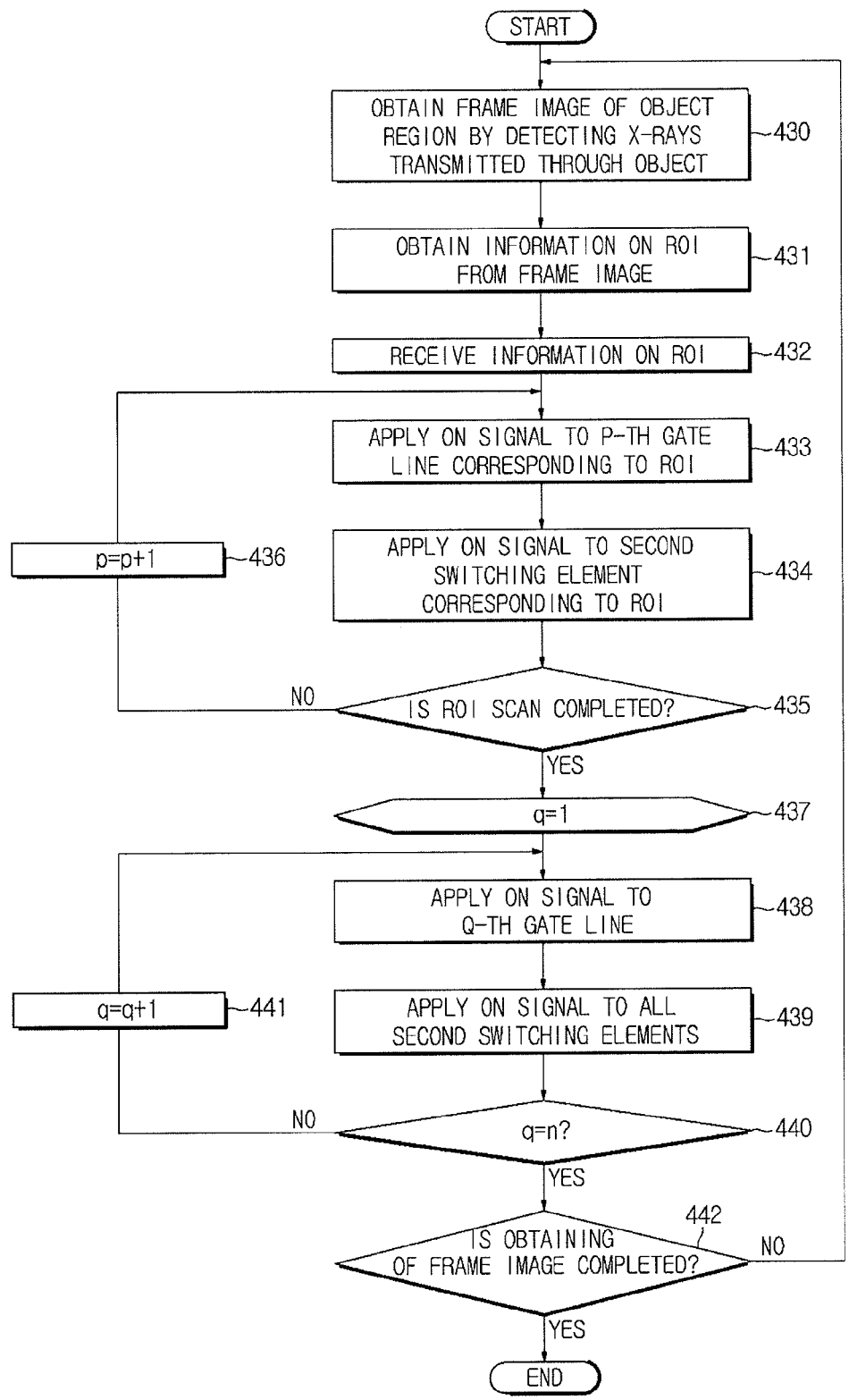
FIG. 18 is a flowchart illustrating a method of controlling an X-ray imaging apparatus according to an exemplary embodiment.

FIG. 18 is a flowchart illustrating a method of controlling an X-ray imaging apparatus according to an exemplary embodiment. The aforementioned X-ray imaging apparatus 200 may be used in the method of controlling an X-ray imaging apparatus according to the exemplary embodiment of FIG. 17, and similarly, the aforementioned X-ray imaging apparatus 200 may also be applied to exemplary embodiment of FIG. 18.

As illustrated in FIG. 18, X-rays are radiated onto the object, X-rays transmitted through the object are detected, and thereby the frame image of the object region is obtained at operation 430. In order to radiate X-rays onto the object, any one of the continuous exposure method and the pulse exposure method may be applied.

Information on the ROI is obtained from the frame image of the object region at operation 431. Obtaining the information on the ROI includes detecting the object of interest and setting the ROI based on the detected object of interest. The information on the ROI includes the position, the size, or the movement characteristic of the ROI and the movement characteristic of the ROI may be defined by the movement characteristic of the object of interest. The information on the ROI may be obtained in real time.

The X-ray detector receives the information on the ROI at operation 432, and the on signal is applied to the p-th gate line corresponding to the ROI at operation 433. When the X-ray detector 100 includes n gate lines, p may be a positive integer equal to or less than n.

Then, the on signal is applied to the second switching element corresponding to the ROI at operation 434. Applying the on signal to the p-th gate line GL(p) and applying the on signal to the second switching element 140 may be performed at the same time or sequentially performed.

When a scan on the ROI is not completed (No in operation 435), a number of a scan target gate line is increased by one (operation 436), and the on signal is applied to a corresponding gate line and second switching element. These operations are repeated until the scan on the ROI is completed.

When a scan on the ROI is completed (Yes in operation 435), a scan is performed on an entire region including the background and the ROI. Specifically, the on signal is applied to a first gate line at operations 437 and 438, and the on signal is applied to all second switching elements, that is, m second switching elements at operation 439. When the scan is not completed up to an n-th gate line (Yes in operation 440), while a number of a scan target gate line is increased by one at operation 441, the on signal is applied to the gate line and the second switching element.

When obtaining of the frame image is completed (Yes in operation 442), the process ends, and otherwise (No in operation 442), the process is repeated starting back at the operation 430 again.

Figure 19:
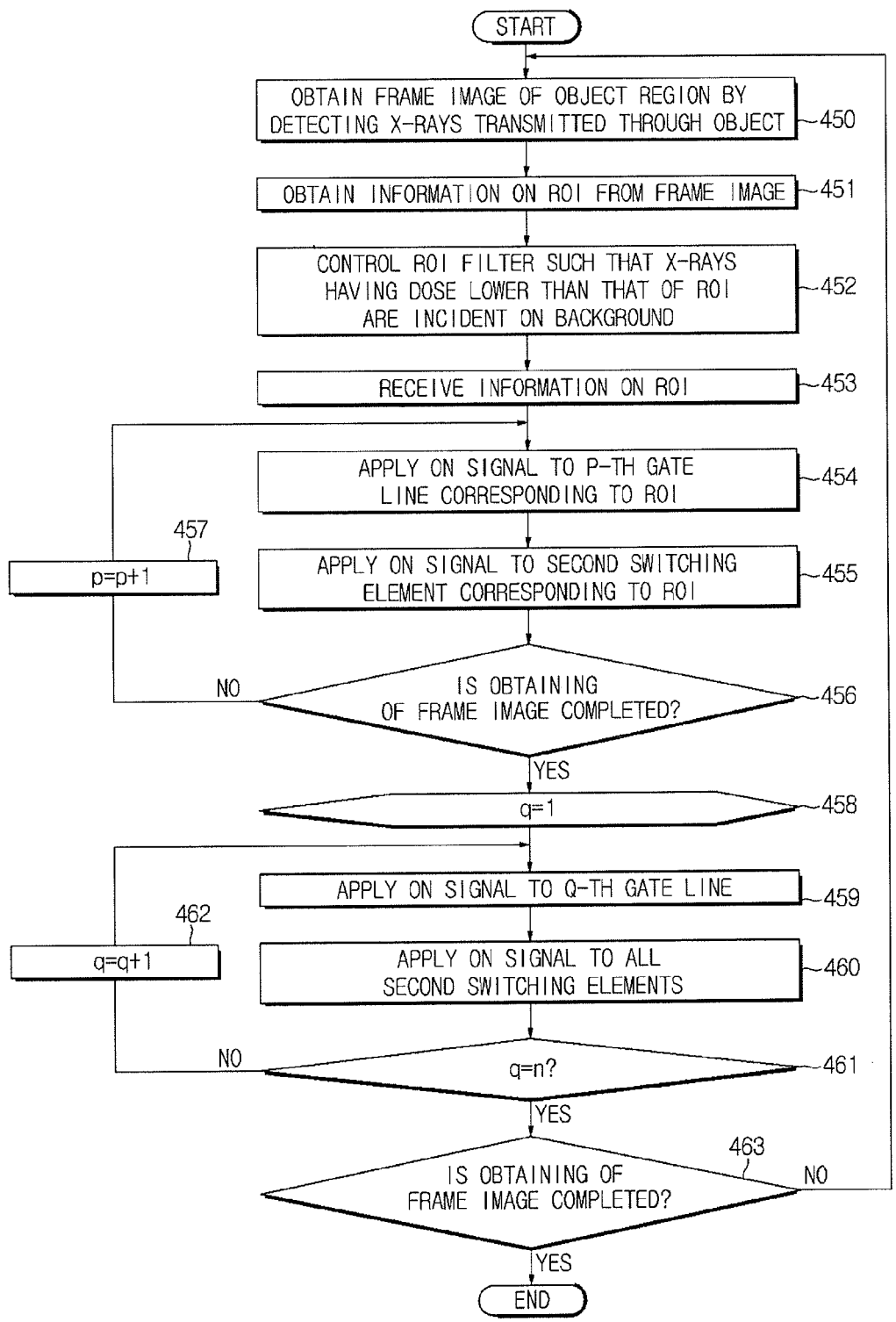
FIG. 19 is a flowchart illustrating a method of controlling an X-ray imaging apparatus which enables low-dose X-rays to be incident on the background according to an exemplary embodiment.

FIG. 19 is a flowchart illustrating a method of controlling an X-ray imaging apparatus which enables low-dose X-rays to be incident on the background according to an exemplary embodiment. The flowchart in FIG. 19 may represent a cycle of an electrical signal read-out at any time point while the frame image is obtained.

As illustrated in FIG. 19, X-rays are radiated onto the object, X-rays transmitted through the object are detected, and thereby the frame image of the object region is obtained at operation 450. In order to radiate X-rays onto the object, any one of the continuous exposure method and the pulse exposure method may be applied.

Information on the ROI is obtained from the frame image of the object region at operation 451. The information on the ROI includes the position, the size, or the movement characteristic of the ROI and may be obtained in real time.

The ROI filter is controlled such that X-rays having a dose lower than a dose of X-rays incident on the ROI are incident on the background at operation 452. As illustrated in FIG. 12, the ROI filter 241 is movably disposed between the X-ray tube 211 configured to radiate X-rays and the X-ray detector 100 configured to detect X-rays. Therefore, the ROI filter 241 is positioned at a position corresponding to the background such that X-rays having a dose lower than a dose of X-rays incident on the ROI are incident on the background. Setting of the ROI may be performed in real time. When the ROI moves, the movement is tracked and the ROI filter 241 moves to the position corresponding to the background.

The X-ray detector receives the information on the ROI at operation 453, and the frame image of the ROI and the frame image of the background are obtained based on the information on the ROI. The frame image of the ROI may be obtained at the first read-out rate, and the frame image of the background may be obtained at the second read-out rate. The first read-out rate may be set based on the movement size of the ROI out of the information on the ROI. The second read-out rate may be set based on the X-ray dose incident on the background. In this exemplary embodiment, the first read-out rate is set to twice the second read-out rate.

In order to obtain the frame image of the ROI and the frame image of the background, the on signal is applied to the p-th gate line corresponding to the ROI at operation 454. When the X-ray detector 100 includes n gate lines, p may be a positive integer equal to or less than n.

Then, the on signal is applied to the second switching element corresponding to the ROI at operation 455. Applying the on signal to the p-th gate line GL(p) and applying the on signal to the second switching element 140 may be performed at the same time or sequentially performed.

When a scan on the ROI is not completed (No in operation 456), a number of a scan target gate line is increased by one at operation 457, and the on signal is applied to a corresponding gate line and second switching element. These operations are repeated until the scan on the ROI is completed.

When a scan on the ROI is completed (Yes in operation 456), a scan is performed on an entire region including the background and the ROI. Specifically, the on signal is applied to a first gate line at operations 458 and 459, and the on signal is applied to all second switching elements, that is, m second switching elements at operation 460. When the scan is not completed up to an n-th gate line (Yes in operation 461), while a number of a scan target gate line is increased by one at operation 462), the on signal is applied to the gate line and the second switching element.

When obtaining of the frame image is completed (Yes in operation 463), the process ends, and otherwise (No in operation 463), the process is repeated starting with the operation of 430 again.

According to the X-ray detector and the method of controlling the same described above, since it is possible to independently read out the electrical signal for each pixel, the read-out rate may be differently applied to each pixel. Accordingly, by applying different read-out rates to the ROI and the non-ROI, it is possible to obtain a high-quality image such that a high read-out rate is applied to the ROI, thereby precisely detecting the movement, and a low read-out rate is applied to the background.

Also, according to the X-ray imaging apparatus and the method of controlling the same described above, the ROI filter is used to enable low-dose X-rays to be incident on the background. As a result, it is possible to reduce X-ray exposure to the object and it is possible to prevent degradation in image quality due to dose reduction by obtaining the frame image of the background at a low read-out rate.

According to aspects of exemplary embodiments, by independently controlling read-out rates of an ROI and a non-ROI, it is possible to decrease X-ray exposure to the object and obtain a high-quality image.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray detector comprising:
   a plurality of pixels which are two-dimensionally arranged and configured to output an electrical signal corresponding to incident X-rays;
   a plurality of gate lines configured to connect the plurality of pixels in a row direction;
   a plurality of data lines configured to connect the plurality of pixels in a column direction;
   a read-out circuit configured to read out the electrical signal generated by the plurality of pixels through the plurality of data lines; and
   a switcher configured to selectively connect between data lines corresponding to a region of interest (ROI) among the plurality of data lines and the read-out circuit.

2. The X-ray detector according to claim 1, further comprising:
   a gate driver configured to apply an on signal to the plurality of gate lines; and
   a switch driver configured to apply an on signal to the switcher.

3. The X-ray detector according to claim 2,
   wherein the switcher comprises a plurality of switching elements configured to be respectively connected to each of the plurality of data lines.

4. The X-ray detector according to claim 3,
   wherein the gate driver is configured to apply an on signal to a gate line corresponding to the ROI among the plurality of gate lines, in order to obtain a frame image of the ROI.

5. The X-ray detector according to claim 4,
   wherein the switch driver is configured to apply an on signal to a switching element to which a data line corresponding to the ROI is connected in order to obtain the frame image of the ROI.

6. The X-ray detector according to claim 5,
   wherein the on signal applied to the gate line and the on signal applied to the switching element are synchronized with each other.

7. The X-ray detector according to claim 6, further comprising
   a detector controller configured to control a timing of the on signal output from the gate driver and the switch driver based on information on the ROI.

8. The X-ray detector according to claim 7,
   wherein the detector controller is configured to control the gate driver and the switch driver such that the frame image of the ROI is obtained at a read-out rate higher than a read-out rate used to obtain a frame image of a background surrounding the ROI.

9. An X-ray imaging apparatus, comprising:
   an X-ray source configured to radiate X-rays onto an object;
   an X-ray detector configured to detect X-rays transmitted through the object among the radiated X-rays, the X-ray detector comprising:
   a plurality of pixels which are two-dimensionally arranged and configured to output an electrical signal corresponding to the detected X-rays,
   a plurality of gate lines configured to connect the plurality of pixels in a row direction,
   a plurality of data lines configured to connect the plurality of pixels in a column direction,
   a read-out circuit configured to read out the electrical signal generated by the plurality of pixels through the plurality of data lines, and
   a switcher configured to selectively connect between data lines corresponding to a region of interest (ROI) among the plurality of data lines and the read-out circuit, to thereby obtain a frame image; and
   an image processor configured to obtain information on the ROI from the frame image obtained by the X-ray detector and deliver the information on the ROI to the X-ray detector.

10. The X-ray imaging apparatus according to claim 9,
    wherein the image processor is configured to detect an object of interest from the frame image and set the ROI based on a position, a size, or a movement characteristic of the object of interest.

11. The X-ray imaging apparatus according to claim 10,
    wherein the information on the ROI includes at least one of a position of the ROI, a size of the ROI, and a movement characteristic of the ROI.

12. The X-ray imaging apparatus according to claim 10, further comprising:
    an ROI filter provided between the X-ray source and the X-ray detector and configured to filter the X-rays;
    a filter driver configured to move the ROI filter; and
    a controller configured to control the filter driver such that the ROI filter moves to a position corresponding to a background of the frame image.

13. The X-ray imaging apparatus according to claim 12,
    wherein the X-ray detector further comprises:
    a gate driver configured to apply an on signal to the plurality of gate lines;
    a switch driver configured to apply an on signal to the switcher; and
    a detector controller configured to control a timing of the on signal output from the gate driver and the on signal output from the switch driver based on the information on the ROI and read-out rates to be applied to the ROI and the background.

14. The X-ray imaging apparatus according to claim 13,
wherein the controller is configured to set a read-out rate to be applied to the ROI based on the information on the ROI and deliver information on the set read-out rate to the detector controller,
wherein the controller is configured to set a read-out rate to be applied to the background based on an X-ray dose incident on the background and deliver information on the set read-out rate to the detector controller.

15. A method of controlling an X-ray detector comprising a plurality of pixels which are two-dimensionally arranged and outputting an electrical signal corresponding to incident X-rays, the method comprising:
receiving information on a region of interest (ROI) of an object based on X-rays transmitted through the object and detected by the X-ray detector;
obtaining a frame image of the ROI at a first read-out rate; and
obtaining a frame image of a background surrounding the ROI at a second read-out rate that is different from the first read-out rate.

16. The method according to claim 15,
wherein the X-ray detector further comprises:
a plurality of gate lines configured to connect the plurality of pixels in a row direction;
a plurality of data lines configured to connect the plurality of pixels in a column direction;
a read-out circuit configured to read out the electrical signal generated by the plurality of pixels through the plurality of data lines; and
a plurality of switching elements connected to each of the plurality of data lines and configured to selectively connect between data lines corresponding to the ROI among the plurality of data lines and the read-out circuit,
wherein the obtaining of the frame image of the ROI comprises:
applying an on signal to a gate line corresponding to the ROI, among the plurality of gate lines, at the first read-out rate; and
applying an on signal to a switching element to which a data line corresponding to the ROI is connected among the plurality of data lines.

17. The method according to claim 16,
wherein the first read-out rate has a value greater than the second read-out rate.

18. A method of controlling an X-ray imaging apparatus, comprising:
radiating X-rays onto an object;
detecting X-rays transmitted through the object among the radiated X-rays and obtaining a frame image of the object based on the detected X-rays;
obtaining information on a region of interest (ROI) from the frame image of the object; and
obtaining a frame image of the ROI and a frame image of a background surrounding the ROI at different read-out rates.

19. The method according to claim 18, further comprising setting a read-out rate to be applied to the ROI based on the information on the ROI.

20. The method according to claim 18, further comprising filtering the radiated X-rays configured to be incident on the background; and
setting a read-out rate to be applied to the background based on an X-ray dose incident on the background.

21. An X-ray detector, comprising:
a detection region comprising a plurality of pixels configured to detect X-rays transmitted through an object and generate corresponding electrical signals based on the detected X-rays;
a switcher configured to independently switch the respective pixels on and off to thereby control read-out rates at which the electrical signals are output; and
a detector controller configured to control the switcher such that pixels corresponding to a region of interest (ROI) of the object output electrical signals at a different read-out rate than a read-out rate at which remaining pixels other than the pixels corresponding to the ROI output electrical signals.

22. The X-ray detector according to claim 21, wherein the switcher comprises a plurality of transistors corresponding to the plurality of pixels.

23. The X-ray detector according to claim 21, wherein information identifying the ROI is input to the detector controller based on frame images captured by the detector controller.

24. The X-ray detector according to claim 21, wherein the read-out rate at which the pixels corresponding to the ROI of the object output the electrical signals is higher than a read-out rate at which the remaining pixels output the electrical signals.

* * * * *